(12) United States Patent
Collier et al.

(10) Patent No.: US 7,540,948 B2
(45) Date of Patent: Jun. 2, 2009

(54) BLOOD UREA NITROGEN (BUN) SENSOR

(75) Inventors: G. Bruce Collier, Fitzroy Habour (CA); Eric Brouwer, Ottawa (CA); Anjulia Wong, Gloucester (CA)

(73) Assignee: Abbott Point of Care Inc., Princeton, NJ (US)

( * ) Notice: Subject to any disclaimer, the term of this patent is extended or adjusted under 35 U.S.C. 154(b) by 0 days.

(21) Appl. No.: 11/216,041

(22) Filed: Sep. 1, 2005

(65) Prior Publication Data

US 2006/0046275 A1 Mar. 2, 2006

Related U.S. Application Data

(60) Provisional application No. 60/606,436, filed on Sep. 2, 2004.

(51) Int. Cl.
*C12M 1/00* (2006.01)
*C12N 9/00* (2006.01)
*C12N 11/00* (2006.01)
*C25B 9/00* (2006.01)
*C12M 1/34* (2006.01)
*C12M 3/00* (2006.01)

(52) U.S. Cl. ............... 204/403.04; 204/403.01; 204/403.02; 204/403.03; 204/403.1; 204/403.11; 204/403.12; 204/403.13; 204/415; 204/403.14; 205/777.5; 205/778; 205/782.5; 435/287.9; 435/288.1; 435/288.3; 435/288.5; 435/12

(58) Field of Classification Search ............... 435/288.3, 435/403.04, 403.14, 287.9, 288.1, 288.5, 435/12; 204/403.04, 403.14, 403.01, 403.02, 204/403.03, 403.1, 403.11, 403.12, 403.13, 204/415; 205/777.5, 778, 782.5

See application file for complete search history.

(56) References Cited

U.S. PATENT DOCUMENTS

| | | | |
|---|---|---|---|
| 4,710,525 A | 12/1987 | Kraemer et al. | |
| 4,713,165 A * | 12/1987 | Conover et al. | 204/403.05 |
| 4,927,516 A | 5/1990 | Yamaguchi et al. | |
| 4,933,048 A | 6/1990 | Lauks | |
| 5,063,081 A | 11/1991 | Cozzette et al. | |
| 5,081,063 A | 1/1992 | Vonno et al. | |
| 5,096,669 A | 3/1992 | Lauks et al. | |
| 5,112,455 A | 5/1992 | Cozzette et al. | |
| 5,200,051 A | 4/1993 | Cozzette et al. | |
| 5,554,339 A | 9/1996 | Cozzette et al. | |
| 5,821,399 A | 10/1998 | Zelin | |
| 5,858,186 A | 1/1999 | Glass | |
| 6,030,827 A | 2/2000 | Davis et al. | |
| 6,143,556 A * | 11/2000 | Trachtenberg | 435/289.1 |
| 6,379,883 B2 | 4/2002 | Davis et al. | |
| 6,673,565 B2 | 1/2004 | LeJeune et al. | |

(Continued)

OTHER PUBLICATIONS

Wall; The Molecular Kinetics of the Urea-Urease System; Arch. Biochem. Biophys.; 43;299-306; (1953).

(Continued)

*Primary Examiner*—William H Beisner
*Assistant Examiner*—Nathan A Bowers
(74) *Attorney, Agent, or Firm*—Katten Muchin Rosenman LLP

(57) ABSTRACT

A BUN (blood urea nitrogen) sensor containing immobilized carbonic anhydrase and immobilized urease for the in vitro detection of urea nitrogen in blood and biological samples with improved performance and precision characteristics.

25 Claims, 14 Drawing Sheets

U.S. PATENT DOCUMENTS 7,041,209 B1 * 5/2006 Pizzariello et al. ....... 205/777.5

OTHER PUBLICATIONS

Taylor; Analytical Reviews in Clinical Biochemistry: the estimation of urea; Ann. Clin. Biochem.; 29; 245-264; (1992).
Nikolelis; Ammonium Ion Minisensors from Self-Assembled Bilayer Lipid Membranes Using Gramicidin as an Ionophore. Modulation of Ammonium Selectivity by Platelet-Activating Factor; Anal. Chem 68; p. 1735; (1996).
Ammann; Ion-Selective Microelectrodes; Springer-Verlag; Berlin; 68-69; (1986).
Botre; Carbonic Anhydrase and Urease: an ivestigation in vitro on the possibility of a synergic action; Biochimica et Biophysica Acta; 997; 111-114; (1989).
Carr; Immobilized Enzymes in Analytical and Clinical Chemistry; John Wiley & Sons, A Wiley-Interscience Publication; 209-211; (1980).
Cesareo; Kinetic Properties of Helicobacter Pylori Urease Compared with Jack Bean Urease; FEMS Microbiol Lett; 99; 15-22; (1992).
Fasman; A Reinvestigation of the Kinetics of the Urease-Catalyzed Hydrolysis of Urea; Journal of the American Chemical Society; vol. 73; 1646-1650; (1951).
Jenkins; Chemical Assay of Urea for Automated Sensing in Milk; J. Dairy Sci.; 82; 1999-2004; (1999).
Steinschaden; Miniaturised Thin Film Conductometric Biosensors with High Dynamic Range and High Sensitivity; Sensors and Actuators; B44; 365-369; (1997).
Suzuki; Fabrication of a Sensing Module Using Micromachined Biosensors; 16; 725-733; (2001).
Nowak; Design, Synthesis, and Evaluation of Bicyclic Peptides as Ammonium Ionophores; Thesis; Worcester Polytechnic Institute; 2003.
Wilbur; Electrometric and Colorimetric Determination of Carbonic Anhydrase; Journal of Biological Chemistry; 176; 147-154; (1948.
Lindskog, S., et al., Carbonic Anhydrase, The Enzymes 5, p. 587, 1971.
Adamson, A. W., A Textbook of Physical Chemistry, Academic Press (New York), Chapter 7, (1973).
Freifelder, D., Physical Biochemistry: Applications to Biochemistry and Molecular Biology, 2nd Ed., W. H. Freeman (San Francisco) 1982, Chapter 4.
Sherwin, J. E. et al., Clinical Chemistry: Theory, Analysis and Correlation, ed. L. A. Kaplan, et al., (St. Louis), 1989, Chapter 21.
Vanderhoff, J. W., J. Poly. Sci. Polymer Symposium 72, p. 161-198 (1985).
C. Botre, et al., "Carbonic Anhydrase Facilitated CO2 Diffusion Studied By Means of An Ammonia Sensing Urease Electrode", Analytical Letters, 22 (11 & 12), 2413-2421, 1989.
European Search Opinion, cf Form 1507, regarding Application No. 05803876.1, 3 pages.
Supplementary European Search Report, regarding Application No. EP 05803876, date of completion of search Sep. 30, 2008.
International Search Report and Written Opinion for the corresponding International Patent Application No. PCT/US2005/031048.

* cited by examiner

—— Standard BUN Sensor
- - - - Bovine serum albumin replaces urease
------- Denatured urease —— Standard Bun Sensor
- - - - Dialyzed urease
------- Enzyme cocktail buffered to pH 7.4, aged 1 week
—·—·— Addition of carbonic anhydrase

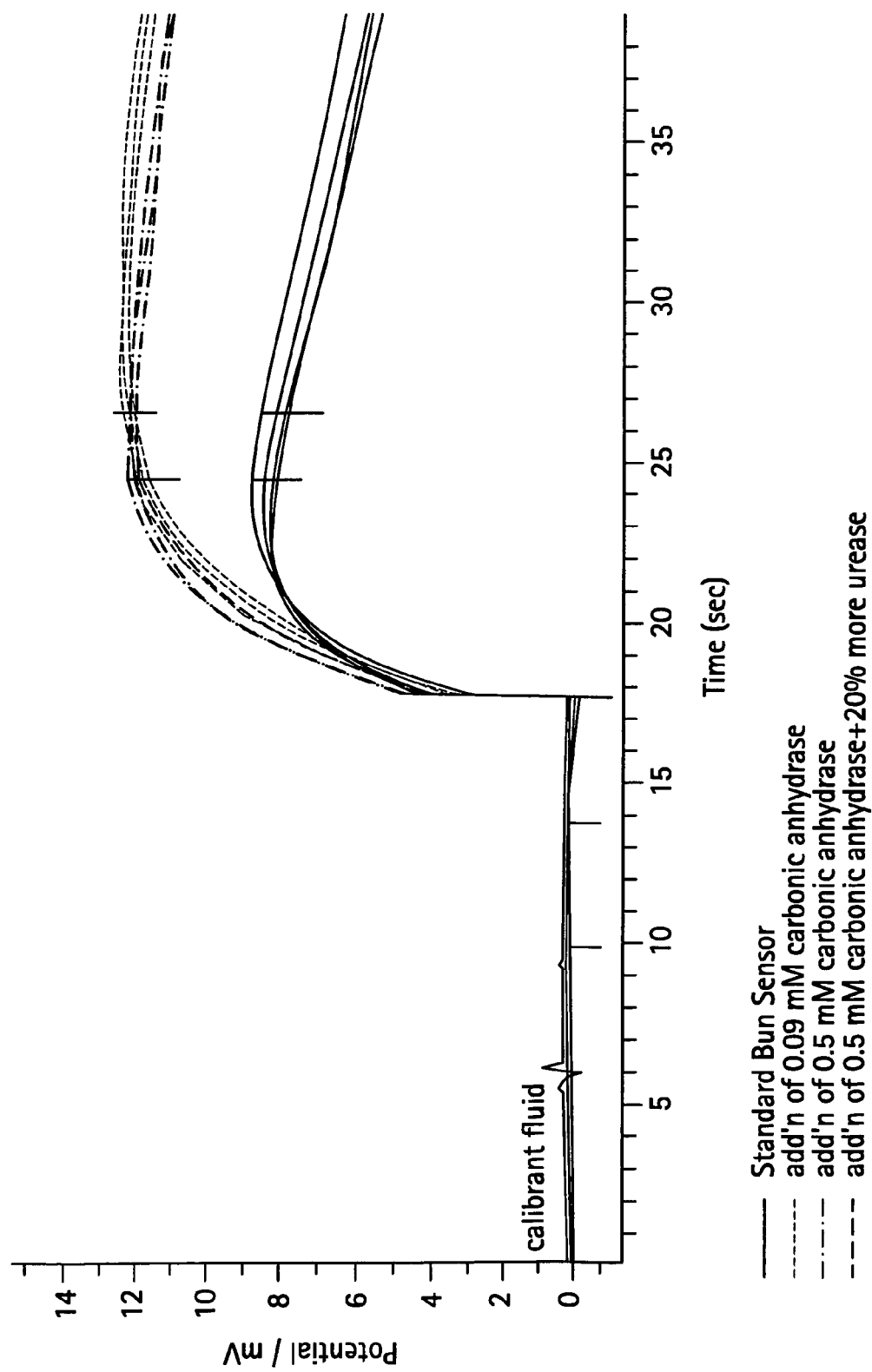

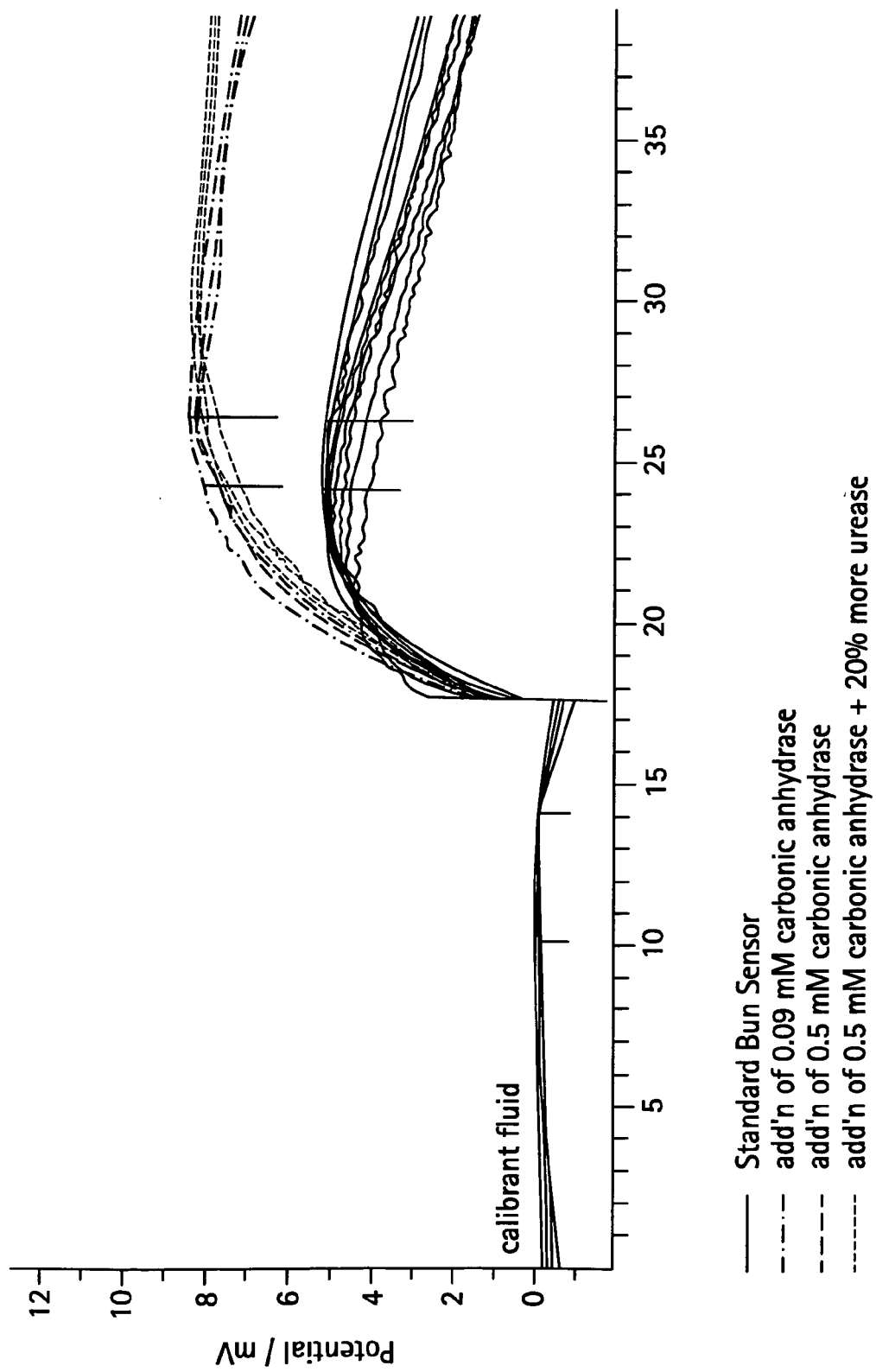

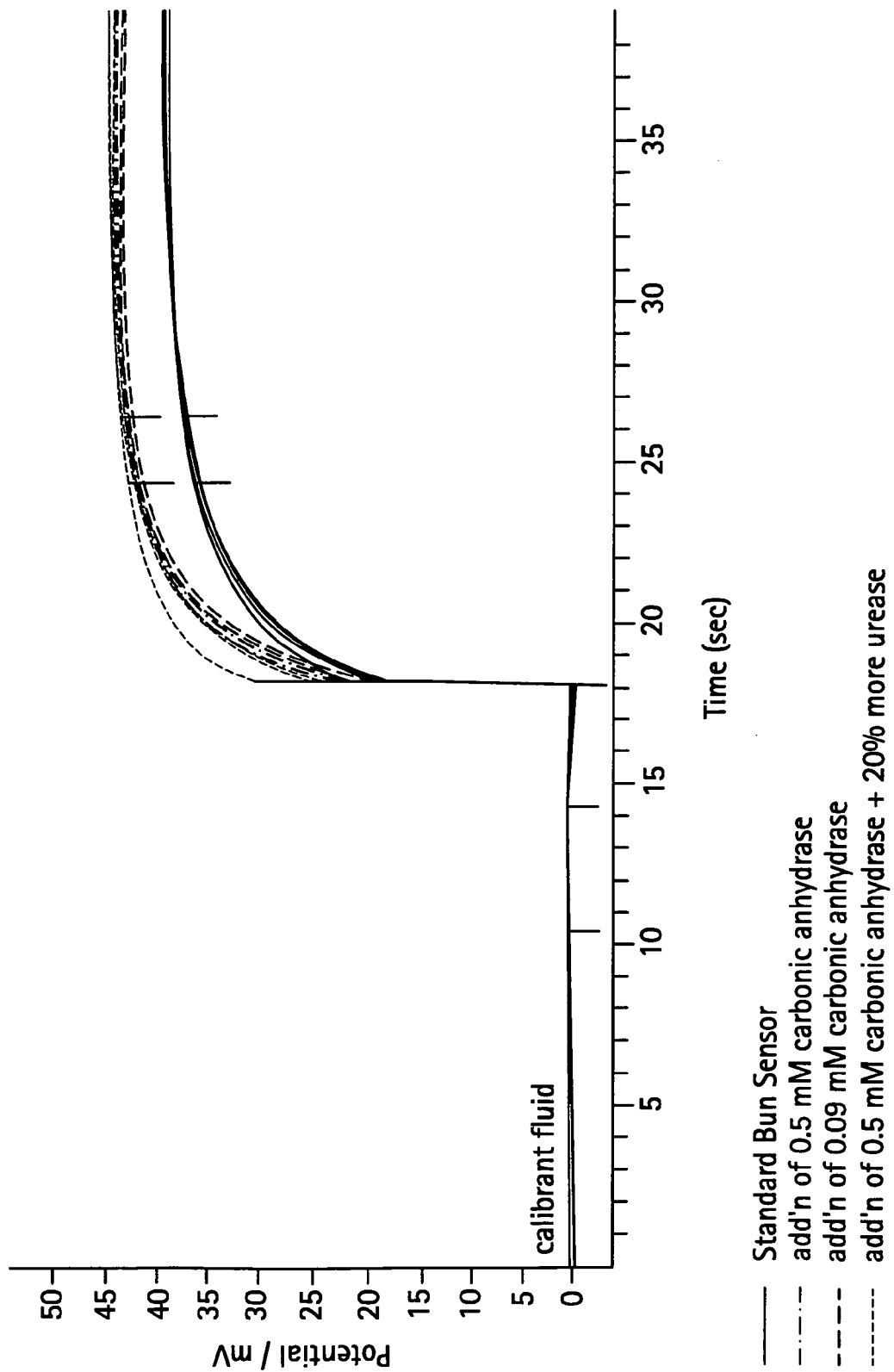

Silver stained SDS-PAGE Protein gel showing the urease enzyme devoid of carbonic anhydrase protein band.

Commercial preparation of urease has no detectable carbonic anhydrase activity.

BLOOD UREA NITROGEN (BUN) SENSOR

This application claims the benefit of priority of U.S. provisional application No. 60/606,436 (filed 2 Sep. 2004).

I. FIELD OF THE INVENTION

An apparatus and method for rapid in situ determination of urea in liquid samples that is capable of being used in the point-of-care clinical diagnostic field, including use at accident sites, emergency rooms, in surgery, in intensive care units, and also in non-medical environments.

II. BACKGROUND OF THE INVENTION

The invention relates to an apparatus and its method of use for determining the presence or concentration of urea in a liquid sample, for example in laboratory autoanalyzers and preferably in single-use disposable cartridges adapted for conducting diverse real-time or near real-time assays of analytes.

In specific embodiments, the invention relates to the determination of urea in biological samples such as blood, blood components and urine.

Micro-fabrication techniques (e.g. photolithography and plasma deposition) are attractive for construction of multilayered sensor structures in confined spaces. Methods for microfabrication of BUN (Blood Urea Nitrogen) sensors, for example on silicon substrates, are disclosed in U.S. Pat. No. 5,200,051 to Cozzette et al., which is hereby incorporated by reference in its entirety. The sensor comprises a silicon chip with a silver/silver chloride electrode over which is a plasticized polyvinylchloride layer containing the ammonium ionophore nonactin. Over this layer is a layer of a film-forming latex material containing urease. Alternative ammonium ionophores include gramicidin D (Nikolelis and Siontorou; Ammonium ion minisensors form self-assembled bilayer, Anal. Chem. 68, 1735, 1996) and bicyclic peptides (Nowak; Design, synthesis and evaluation of bicyclic peptides as ammonium ionophores; Thesis, Worcester Polytechnic Institute, 2003).

The Cozzette et al., device operates in the standard potentiometric manner, where the enzyme urease converts urea from the sample to ammonium ions, these ions are detected by the ammonium-selective membrane covering the electrode. The electrical potential at the electrode is a logarithmic function of the ammonium concentration and thus the bulk urea concentration. By calibrating the sensor with known standards containing urea, the urea concentration in the sample can be estimated.

The enzyme carbonic anhydrase (CA) has been used in a carbon dioxide ($pCO_2$) sensor, where it was added to the electrolyte layer to accelerate the $CO_2/H_2CO_3$ aqueous equilibrium. This use of CA is well known and unrelated to urea sensing, see: Lindskog, S., Henderson, L., Kannan, K., Liljas, A., Nyman, P., and Strandberg, B.: Carbonic Anhydrase, *The Enzymes* 5, 587, 1971.

Botre, C. and Botre, F., ("Carbonic Anhydrase and Urease: An Investigation In Vitro on the Possibility of Synergic Action,") Biochimica et Biophysica Acta, 997, 111-4, (1989), contains support for there being a physiological linkage between in vivo levels of urea and the production of CA enzyme activity. Botre teaches that placing an ammonia gas-sensing electrode, a carbon dioxide gas-sensing electrode, and a pH sensor into a solution containing either urease, or urease and carbonic anhydrase. It also teaches the addition of urea and a CA inhibitor (acetazolamide) to the solutions. These experiments are consistent with predictions based on the law of mass action, which are that the presence of carbonic anhydrase can influence (increase) the rate of hydrolysis of urea by urease, since CA effectively removes carbon dioxide from the system by moving it into the gas phase.

Specifically, the bicarbonate formed by the urease reaction is converted to carbon dioxide by CA, which then diffuses out of the liquid phase and into the air. This process has the effect of reducing the back reaction in which ammonium ions plus bicarbonate are converted to urea. Thus the net effect of the presence of CA in this system is to increase the rate of ammonium ion production.

Regarding the law of mass action, it is well known in the art of reversible enzymatic reactions, generically A=B+C, to add a reagent D which reacts with C, for the purpose of driving the reversible reaction in the direction of B (A. W. Adamson, A Textbook of Physical Chemistry, Academic Press (New York) 1973, chapter 7.). While the present invention also seeks to use carbonic anhydrase to influence the reactivity of urease (UR), Botre does not suggest the present invention for at least the following reasons:

Botre is silent on analytical determination of the concentration of urea in a sample, and silent on analytical determination of urea in biological samples of clinical interest, e.g. a blood sample. Botre is also silent on the immobilization of UR and CA, as well as on potentiometric electrodes with immobilized enzymes.

Botre is silent on microfabrication of potentiometric electrodes for determining any analyte including urea, and on the use of the enzymes UR and CA in a system which does not permit the exchange of carbon dioxide from solution to an air space, as in a cartridge of the U.S. Pat. No. 5,096,669 incorporated herein their entirety by reference and other analytical systems where urea is measured electrochemically.

The concept of differential electrochemical e.g. potentiometric and amperometric, measurement is well known in the electrochemical art, see for example Cozzette, U.S. Pat. No. 5,112,455 and Cozzette, U.S. Pat. No. 5,063,081, both incorporated herein by reference in their entirety.

U.S. Pat. No. 5,081,063 discloses the use of permselective layers for electrochemical sensors and the use of film-forming latexes for immobilization of bioactive molecules, incorporated herein by reference. The use of poly(vinyl alcohol) (PVA) in sensor manufacture is described in U.S. Pat. No. 6,030,827 incorporated by reference. U.S. Pat. Nos. 6,030,827 and 6,379,883 teach methods for patterning poly(vinylalcohol) layers and are incorporated by reference in their entirety.

Gel electrophoresis of a typical commercial urease preparation, as shown in FIG. 14, indicates that prior art BUN sensors would not have included Carbonic Anhydrase as a significant impurity.

III. SUMMARY OF THE INVENTION

One object of the invention is to provide a device for detecting urea in a sample, comprising: (a) a sensor to which a sample suspected of containing urea may be brought into contact, the sensor including at least two enzymes, urease and carbonic anhydrase immobilized on at least a portion of said sensor, and (b) a detector system for processing signals from the sensor.

Another object is to provide a sensor membrane comprising: a water-permeable matrix, including at least two enzymes, urease and carbonic anhydrase.

Another object is to provide a device for detecting urea in a sample, comprising: an electrode coated with a first layer, said first layer comprising plasticized polyvinyl chloride and nonactin, and at least two enzymes, urease and carbonic anhydrase, immobilized on said first layer.

Another object is to provide a device for detecting urea in a sample, comprising: an electrode coated with a first layer, said first layer comprising plasticized polyvinylchloride and nonactin, and a second layer positioned over and contacting at least a portion of said first layer, said second layer comprising a water-permeable matrix and including at least two enzymes, urease and carbonic anhydrase.

Another object is to provide a microfabricated sensing device for detecting urea in a sample, comprising: (a) a substantially planar substrate having a patterned microelectrode surface, (b) a first layer over at least a portion of said substrate comprising a plasticized polymer and nonactin, and (c) a second layer over at least a portion of said first layer, comprising a water-permeable matrix including at least two enzymes, urease and carbonic anhydrase.

Another object is to provide an improved ion-selective sensor for detection of urea having a layer in which is immobilized an enzyme, urease, the improvement comprising: immobilizing at least one other enzyme, carbonic anhydrase, in said layer.

Another object is to provide a method for assaying urea in a sample, comprising: contacting a sample suspected of containing urea with a sensor having at least one layer and at least two enzymes, urease and carbonic anhydrase, immobilized in said at least one layer, and detecting a chemical moiety in proximity to said at least one layer with a sensor selected from the group consisting of an ammonium ion sensor, a pH sensor, a carbon dioxide sensor, and a bicarbonate sensor.

Another object is to provide a method for improving the sensitivity of a urea sensor, which sensor comprises a detector and at least one layer in which is immobilized an enzyme, urease, the method comprising: immobilizing an effective amount of a second enzyme, carbonic anhydrase, in said at least one layer.

IV. BRIEF DESCRIPTION OF THE DRAWINGS

FIG. 4 shows the response curves to buffered aqueous control fluids (M1=50 mM urea; P1=20 mM urea) using different BUN sensor designs. Top: standard BUN sensor; BUN sensor with denatured urease; BUN sensor with protein (bovine serum albumin) replacing urease. Bottom: standard BUN sensor; BUN sensor with enzyme layer buffered to 7.4 and aged 1 week; BUN sensor with addition of carbonic anhydrase; BUN sensor with dialyzed urease.

FIG. 5 shows whole blood response curves, day 1, for BUN sensors with modifications to enzyme layer.

FIG. 6 shows whole blood response curves, after 4 days cartridge incubation at 40° C., for BUN sensors with modifications to enzyme layer.

FIG. 7 shows buffered aqueous control fluid (M1=50 mM urea) response curves, after 4 days incubation at 40° C., for BUN sensors with modifications to enzyme layer. Modified BUN sensors with additional carbonic anhydrase exhibit increased signal.

Figure 8:
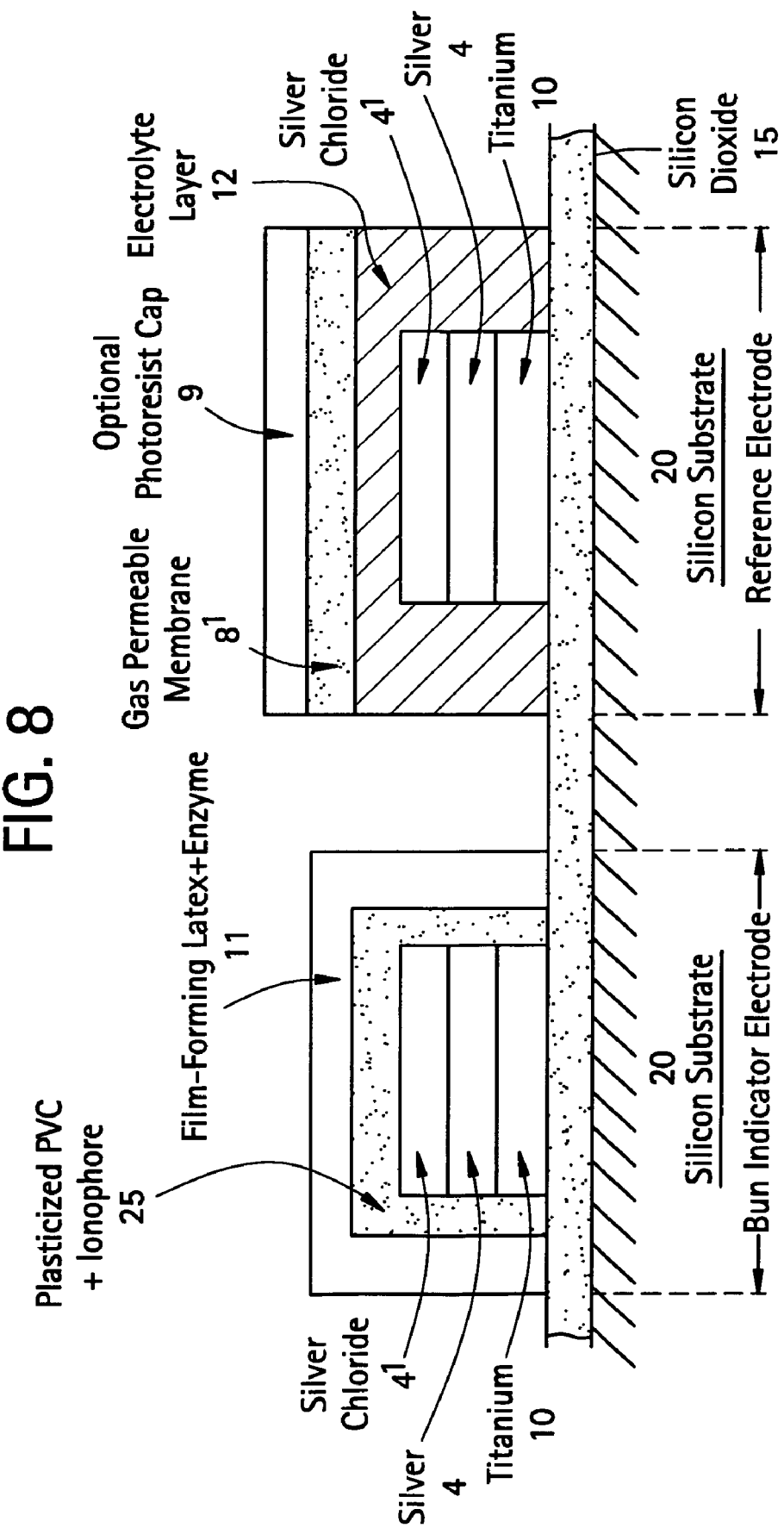

FIG. 8 is a topological schematic side elevation of a potentiometric blood urea nitrogen (BUN) sensor and reference electrode.

Figure 9:
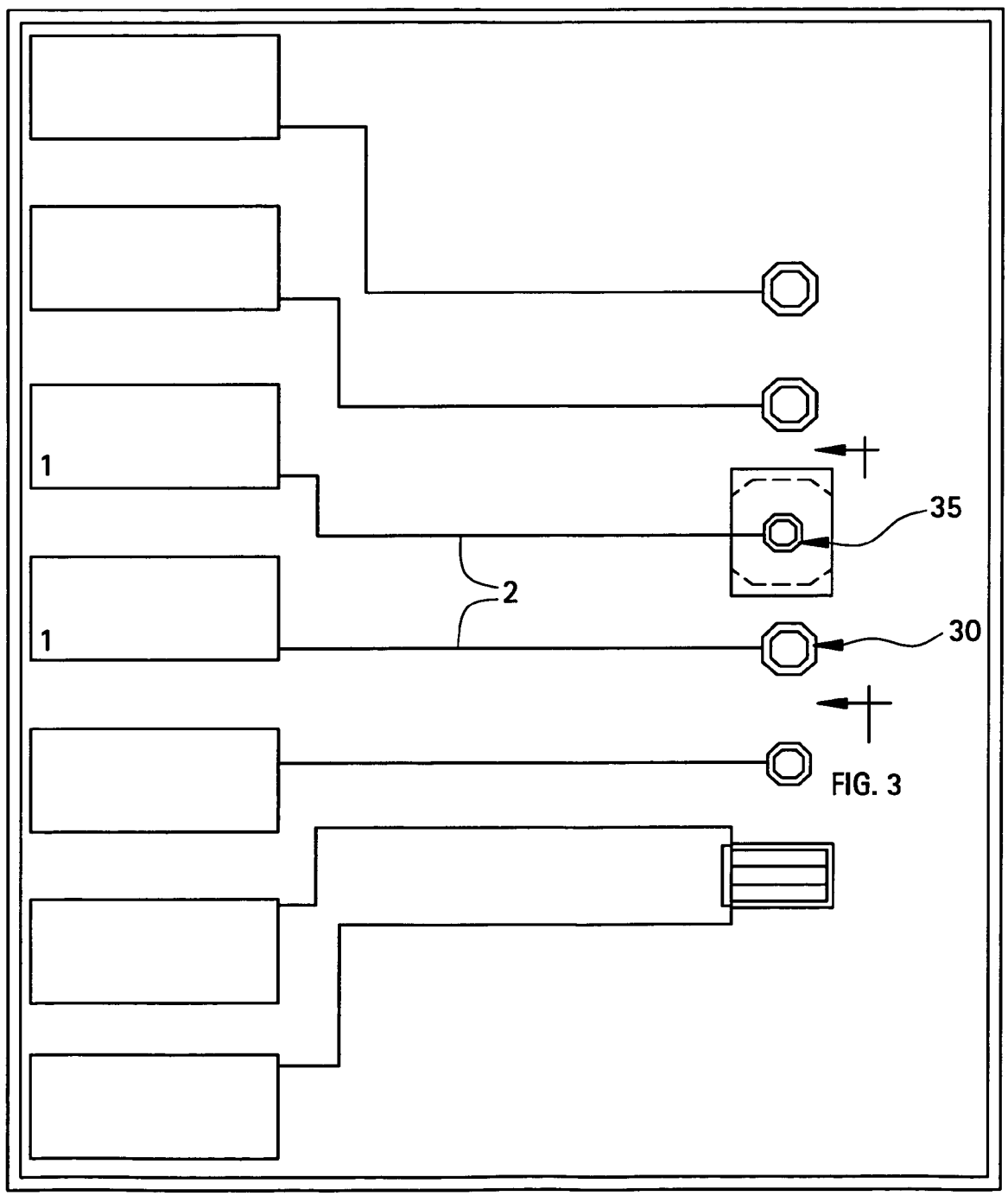

FIG. 9 is the top elevation of the sensor of FIG. 8, showing an array of different sensors on a single chip.

Figure 10:
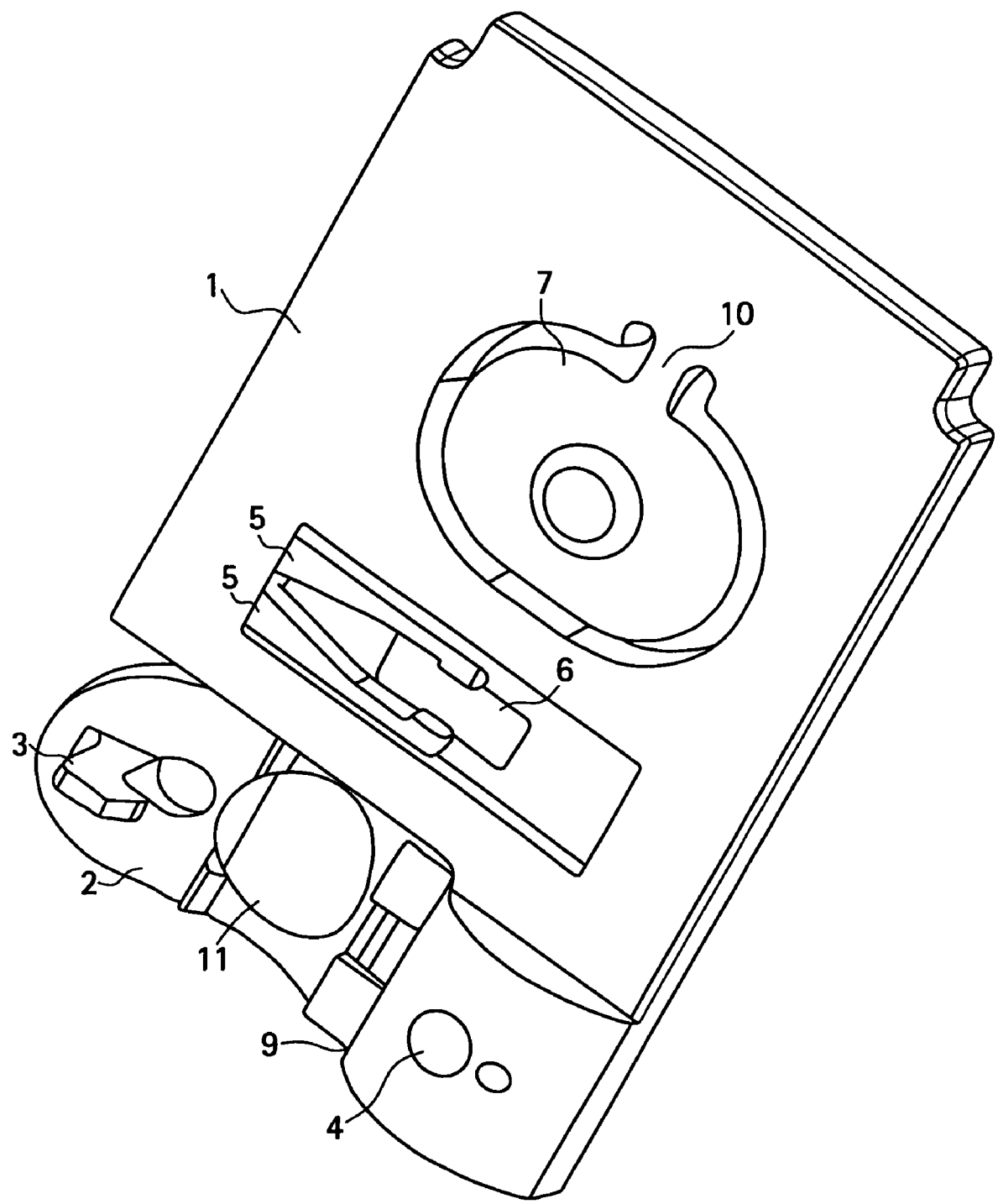

FIG. 10 is an isometric top view of a sensor cartridge cover.

Figure 11:
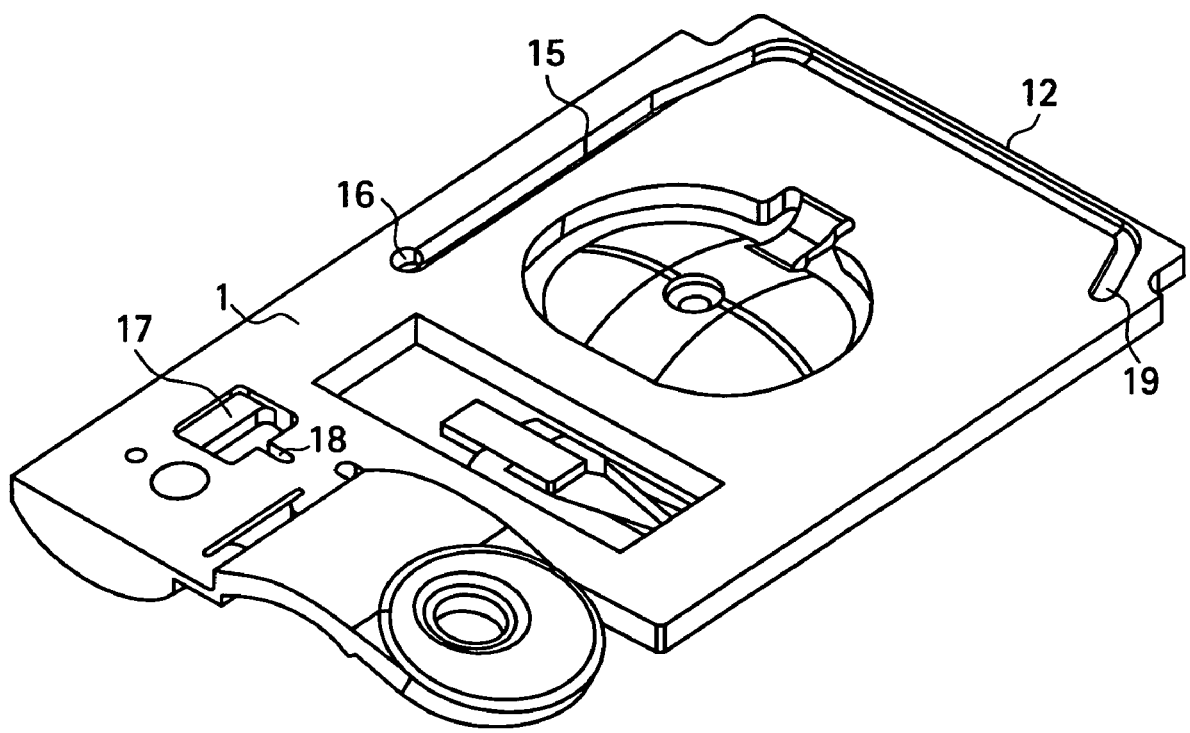

FIG. 11 is an isometric bottom view of a sensor cartridge cover.

Figure 12:
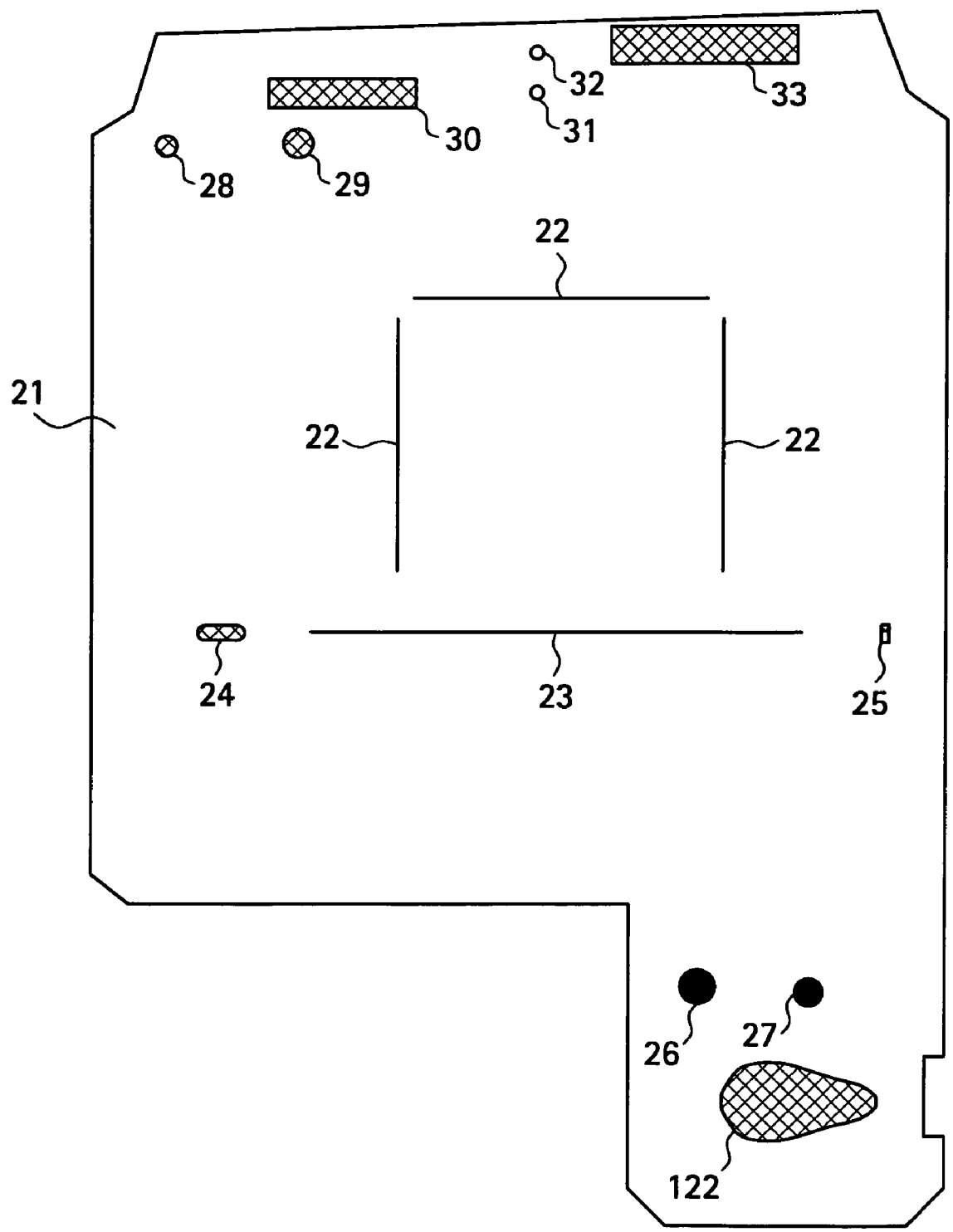

FIG. 12 is a top view of the layout of a tape gasket for a sensor cartridge.

Figure 13:
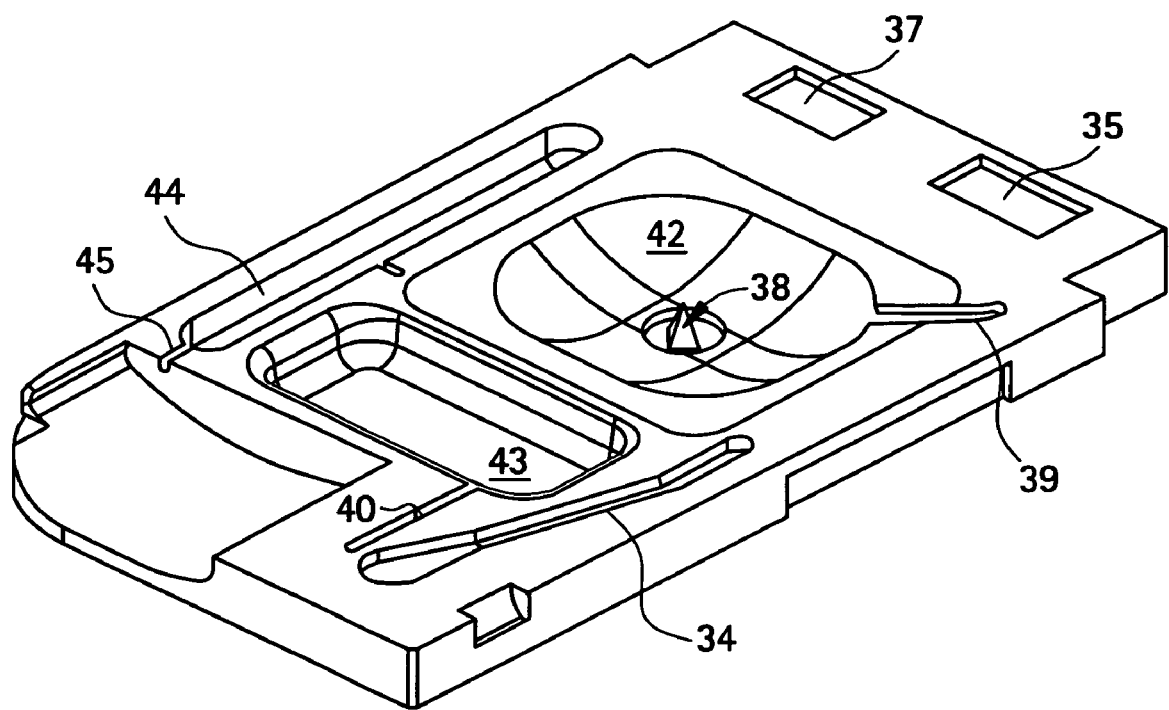

FIG. 13 is an isometric top view of a sensor cartridge base.

Figure 14:
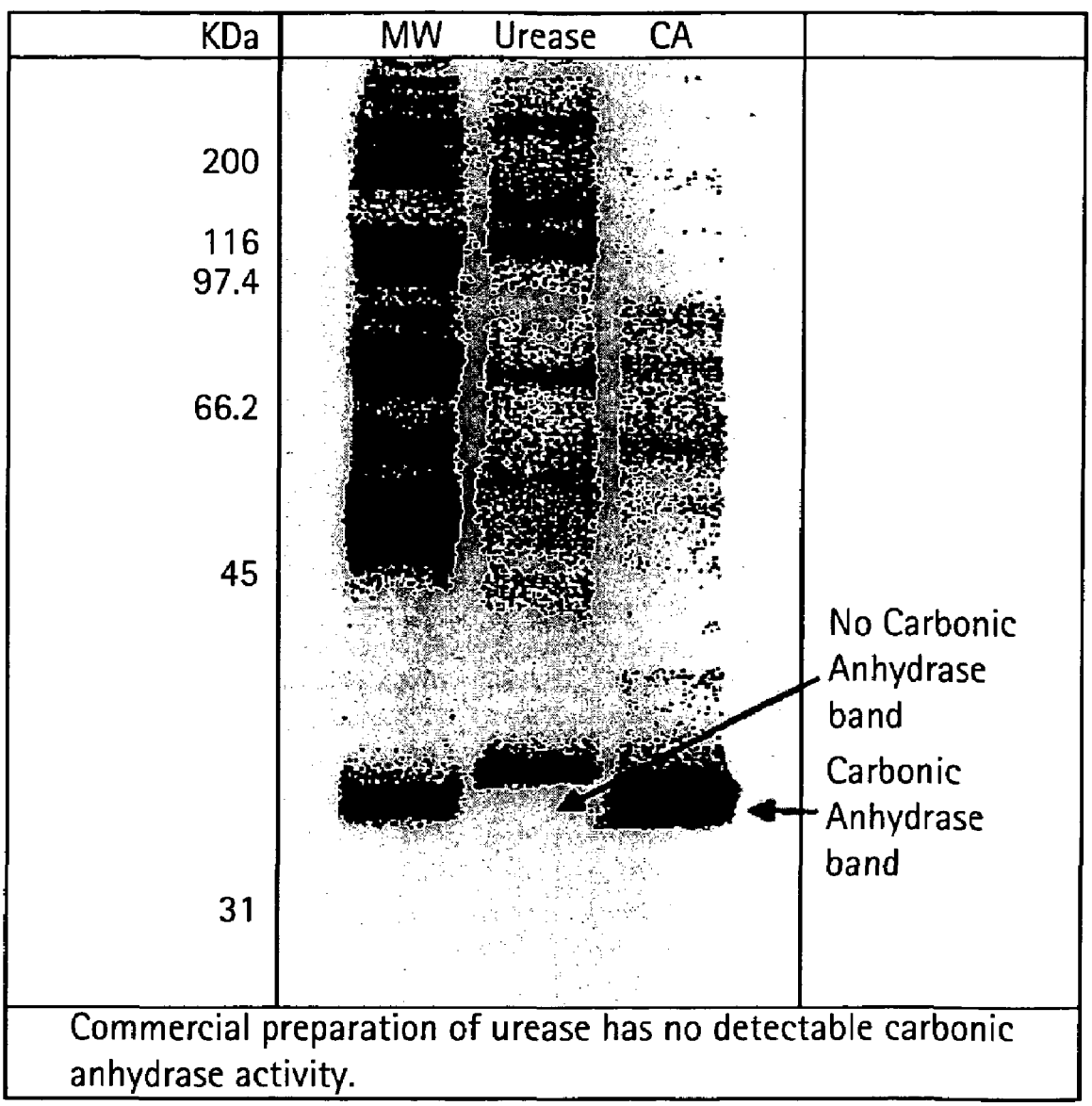

FIG. 14 is a silver stained SDS-PAGE protein gel with a molecular weight marker, commercially available urease, and commercially available carbonic anhydrase.

V. DETAILED DESCRIPTION OF THE INVENTION

The present invention permits rapid in situ determinations of urea using a cartridge having an array of analyte sensors and means for sequentially presenting a sample and a fluid (amended or not) to the analyte array. The cartridges are designed to be preferably operated with a reading device, such as that disclosed in U.S. Pat. No. 5,096,669 to Lauks et al., issued Mar. 17, 1992, or U.S. Pat. No. 5,821,399 to Zelin, issued Oct. 13, 1998, which are both hereby incorporated by reference in their respective entireties.

The invention will be discussed primarily in terms of application to the -i-STAT system, e.g., the cartridge and analyzer disclosure in Lauks et al., U.S. Pat. No. 5,096,669. However, one skilled in the art will recognize that the invention can be used more broadly, for example in other single-use disposable sensor formats, in limited multi-use sensor cartridge formats, and in analyzers having sensors that are used and recalibrated until they fail and are replaced, or in which a membrane component containing the enzyme reagents is replaced. These assay formats are well known commercial alternatives in the electrochemical sensing art.

In the -i-STAT system a BUN sensor, along with several other sensors, first contacts a calibrant fluid and then a blood sample. The role of the calibrant is to provide a single solution that acts as a universal standard of known concentration for each of the sensors. One skilled in the art will recognize that selecting its composition will require a trade-off between the competing needs of individual sensors, e.g. in terms of buffer salt selection, buffer concentration, pH, ionic strength, reagent stability and the like.

The BUN assay is useful to physicians assessing the health of their patients. It measures the level of urea nitrogen in the blood, which is a waste product of protein metabolism cleared by the kidneys. Therefore, it assesses renal function. Typical BUN values are 8-20 mg/100 ml. The condition known as azotemia, i.e. increased BUN levels, can indicate impaired renal function, congestive heart failure, dehydration, shock, hemorrhage into the gastrointestinal tract, stress, acute myocardial infarction or excessive protein intake. Alternatively, decreased BUN values may indicate liver failure, malnutrition, anabolic steroid use, pregnancy and siliac disease.

Urea, $NH_2C(O)NH_2$, in whole blood is detected by the -i-STAT BUN sensor in a two-step process. First, the urea is enzymatically converted to the products $NH_4^+$ and $HCO_3^-$, via a complicated mechanism that is not well understood. There are several different representations of the enzymatic decomposition of urea found in the literature (Steinschaden, (1997) *Sensors and Actuators* B44, 365-369; H. Suzuki (2001) *Biosensors and Bioelectronics* 16, 725-733; A. J. Taylor (1992), *Ann. Clin. Biochem.* 29, 245-264; D. M. Jenkins (1999) *J. Dairy Sci.* 82, 1999-2004). Two typical representations of the reaction, are given below:

$$(NH_2)_2CO + H_2O \rightleftharpoons 2NH_3 + CO_2 \quad (1)$$

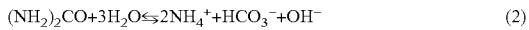

$$(NH_2)_2CO + 3H_2O \rightleftharpoons 2NH_4^+ + HCO_3^- + OH^- \quad (2)$$

The second step in the detection of urea is the potentiometric determination of ammonium ion activity by the $NH_4^+$ ion-selective electrode (ISE). It is acceptable to approximate the activity of $NH_4^+$ to be its concentration. This is well known in the electrochemical art (D. Freifelder, *Physical Biochemistry: Applications to Biochemistry and Molecular Biology*, $2^{nd}$ ed., W.H. Freeman (San Francisco) 1982, chapter 4). The BUN sensor response, i.e. change in potential due to changes in the concentration of $NH_4^+$, is calibrated at known levels of urea in blood. The plot of the -i-STAT sensor response curve, mV as a function of time, thus indicates the concentration of ammonium ion within the sensor membrane, which provides an estimate indirectly of the urea concentration in blood.

The urease enzyme reaction can also be detected by sensors for the moieties $H^+$, $CO_2$ and $HCO_3^-$ because these are produced or consumed in the reaction. Detection of ammonium ion is preferred because the blood has a significant background of $H^+$, $CO_2$ and $HCO_3^-$, which would generally require a differential measurement (i.e., taking the difference between an enzyme-coated sensor and an adjacent bare sensor), while the ammonium background level in blood is comparatively low. The production of ions during the urease reaction also increases the conductivity of the sample, which can be detected with a conductivity sensor. Again, since the sample has a high background conductivity, this is not the preferred detection method. Sensors for pH, $CO_2$, $HCO_3^-$ and conductivity are well known in the electrochemical sensing art.

The conversion of urea to ammonium ion and carbon dioxide or to carbonium ion affects the local pH of the immobilized urease enzyme. It is known that urease has a pH optimum around pH 6 to pH 7.5. Deviations from this pH range will reduce enzyme activity, which in turn can affect the linearity of response of the sensor at the higher substrate concentrations. Changes of pH in the matrix used to immobilize the enzyme can also have significant effects on enzyme performance. This can be observed for manufactured sensors, in terms of sensor shelf-life.

Figure 1:
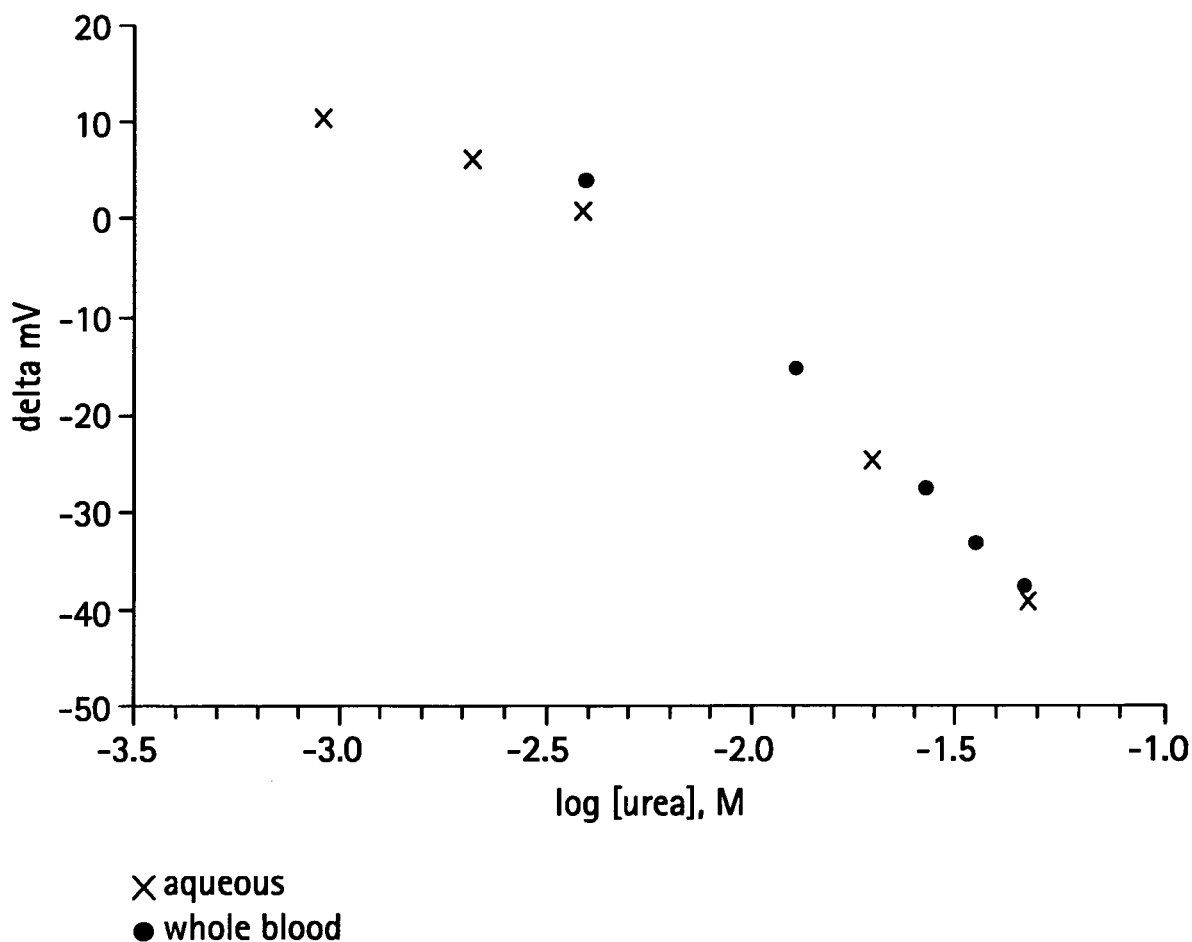
FIG. 1 shows Nernst plot of a prior art sensor response, in mV, as a function of log [urea], in M, over the range of 1 to 90 mM urea, for (–) aqueous and (•) whole blood.
Figure 2:
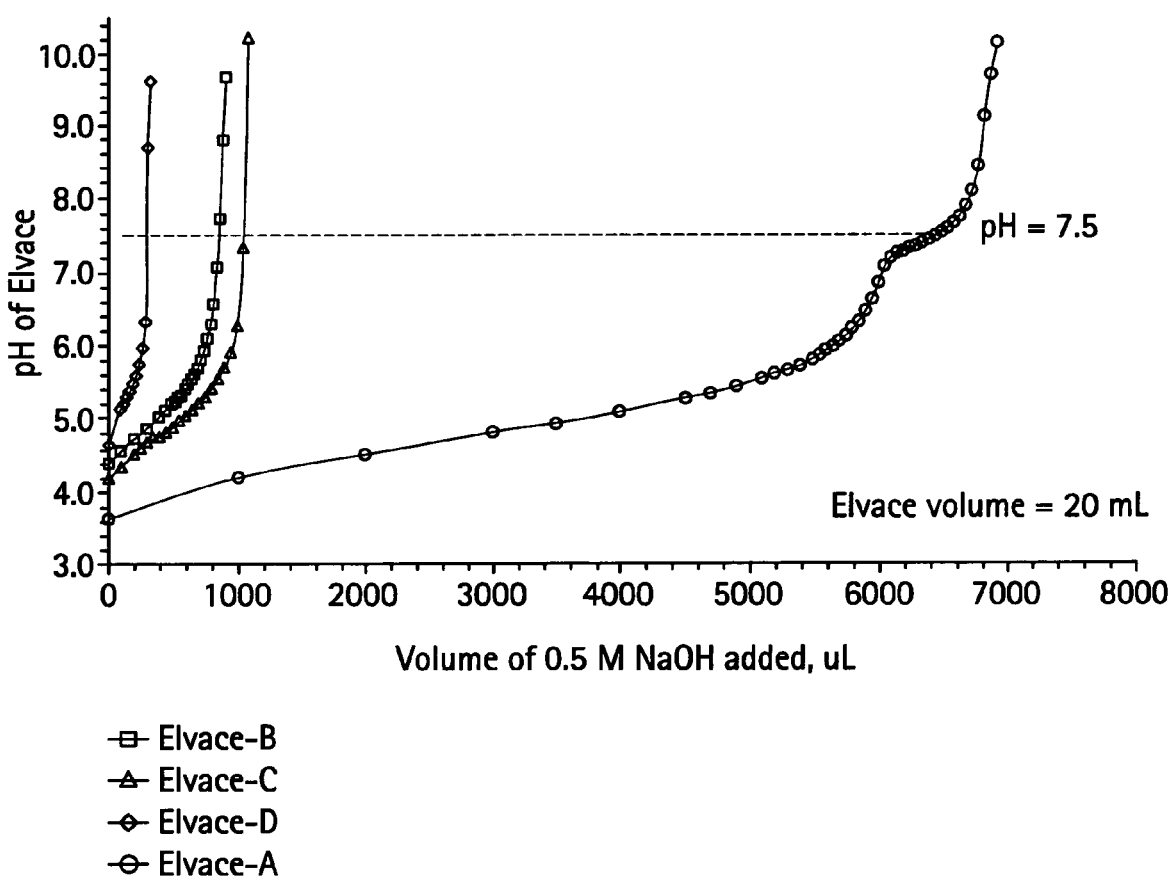
FIG. 2 shows a 0.5 M NaOH pH titration of different Elvace polymer lots (volume=20 mL), indicating buffering capacity at pH 7.5 for lot A. The remaining Elvace lots do not exhibit buffering capacity at pH 7.5.
Figure 3:
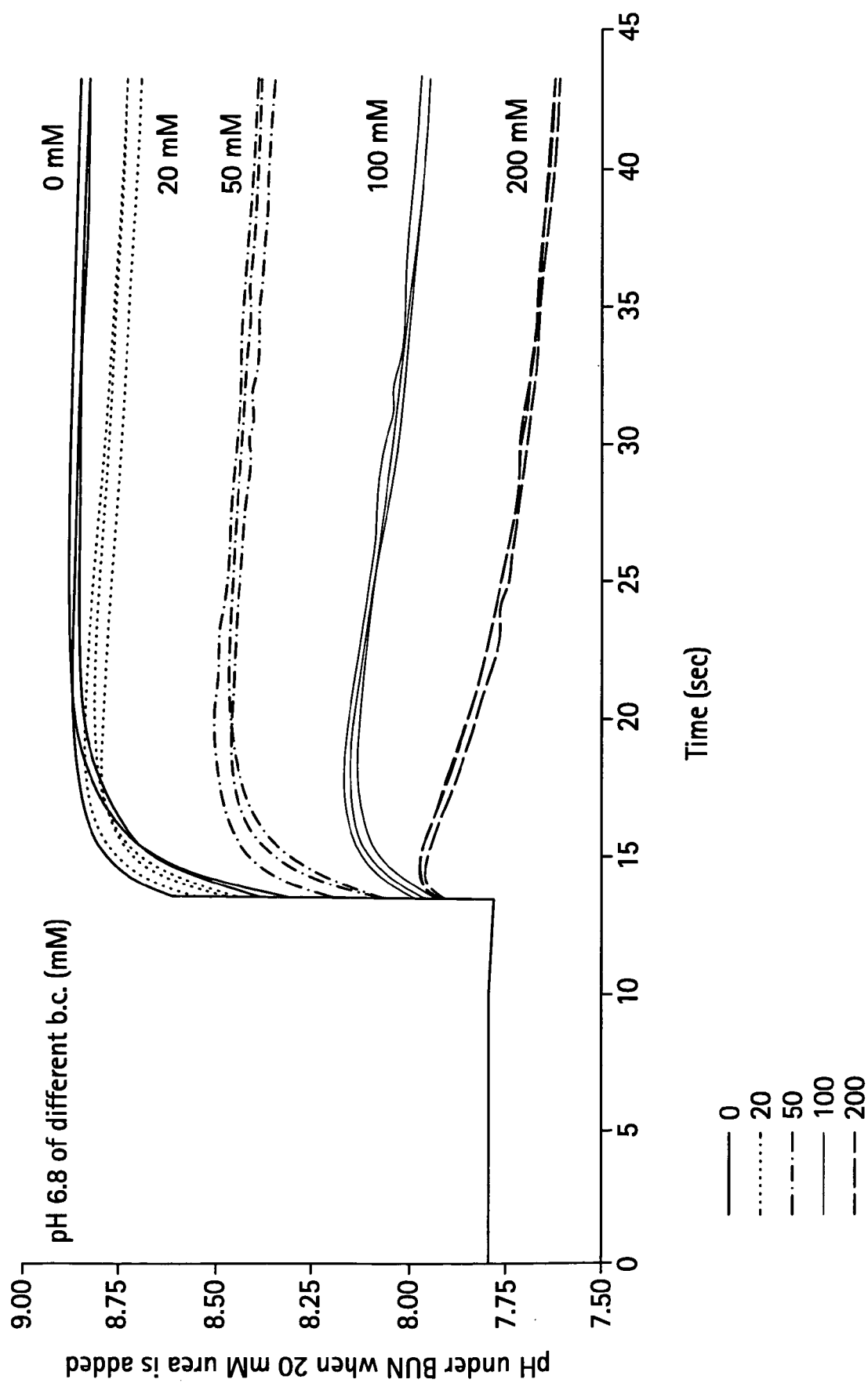
FIG. 3 shows internal pH of the urease-containing Elvace layer after contact with urea-containing calibrant solution (t<10 s). Samples (t>14 s) with high buffer capacity maintain a consistent internal pH. (In the figure, b.c. refers to the sample buffer capacity).

Output characteristics of a BUN sensor containing only the urease enzyme: The BUN sensor linearity of a prior art design (U.S. Pat. No. 5,200,051) is shown in FIG. 1. These are Nernst plots of the sensor response, in millivolts (mV), as a function of log [urea], over the range of 1 to 90 mM urea.

The typical clinical reportable range is 1-50 mM (at 50 mM, log [urea]=−1.3). As with all sensors, the response does not quite meet the theoretical linear behavior, especially at the low end of the analyte range. While the theoretical Nernst slope is about 59 mV/decade at ambient temperature, this BUN design exhibits approximately 37 mV/decade at the high (linear) end. Note that as long as the expected slope for a manufactured batch of sensors is known, it can be programmed into the software that runs the sensor test cycle. This value, rather than the theoretical value of the slope, is then used in calculations. A detailed description of well-known equations and calculations used in the operation of sensors of this type is given in U.S. Pat. No. 5,112,455, fully incorporated herein by reference.

The present invention will be better understood with reference to the specific embodiments set forth in the following Examples.

1. Enzyme Immobilization and Sensor Performance

This example deals with ways in which enzymes are immobilized on a base sensor in a manner that retains enzymatic activity. The preferred material is ELVACE®, which is a commercially-available adhesive consisting of a water-based emulsion of the copolymer poly(ethylene)(vinylacetate). It is used as the water-permeable matrix (termed BUN cocktail) for immobilizing the enzymes.

We have found that adding sodium phosphate buffer (pH ~6.5, 6.8 and pH 7.4) to the BUN cocktail improves its buffering capacity. This results in the usable life of the cocktail, i.e. the time from preparation to application (e.g. microdispensing it onto the sensor surface), being increased from about 16 hours up to about 25 days. Microdispensing, as an application method, is disclosed in jointly owned U.S. Pat. No. 5,554,339, fully incorporated by reference.

Using either 50, 75 or 100 mM sodium phosphate buffer at pH 7.4, we observed that reliable printing was maintained for up to about 25 days, based on visual assessment of the printed material on the sensor and sensor performance.

It is known that urease in enzyme activity assays has significantly reduced activity at pH values above pH 7.4. Urease enzyme activity at pH 8.0 is typically about 50% that of pH 7.0. Secondly, a greater sensor response at high [BUN] is observed with the added buffer. The reasons for the sensor response improvement are discussed below.

It is well known that jack bean (*Canavalia ensiformis*) urease activity is both buffer and pH-dependent; the optimal pH for urease in TRIS buffer is between pH 6.0 and pH 8.0 (Cesareo, S., and Langton, S.: Kinetic Properties of *Helicobacter-Pylori* Ureases Compared with Jack Bean Urease, *FEMS Microbiol Lett* 99, 15, 1992). In the prior art -i-STAT system, the calibrant fluid has a pH of 7.4, however in the localized region of the BUN sensor, i.e. the BUN matrix and its diffusion layer, the pH may be elevated to about pH 7.85 due to the production of hydroxide ion (OH—) from enzymatic degradation of urea in the calibrant fluid by urease in the matrix. When the BUN sensor is contacted with the blood sample, typically at pH 7.4, it is known that pH buffering is dominated by hemoglobin (J. E. Sherwin and B. B. Bruegger in *Clinical Chemistry: Theory, Analysis and Correlation*, ed. L. A. Kaplan and A. J. Pesce, C. V. Mosby (St. Louis), 1989, Chapter 21). This can result in a different pH in the region of the BUN sensor. These non-optimal pH values in the region of the sensor may affect the product distribution, lower the sensor response and increase variability. It has been found that addition of the sodium phosphate buffer to the BUN cocktail significantly improves buffering of urease in the matrix, and reduces the difference in behavior between aqueous calibrant fluids and whole blood samples.

We have found that adding sodium phosphate buffer (pH 6.0, 6.8 and pH 7.4) to the BUN cocktail for microdispensing improves the solubility of the enzyme in that buffer.

Another way to decrease the sensor response time (the time to reach 95% of the steady state signal) was discovered by determining if the sensor response is rate-limited by the formation of $NH_4^+$. Carbonic anhydrase (CA) was added to the enzyme matrix to remove bicarbonate/carbon dioxide by forming the carbonate anion ($CO_3^{2-}$), thus pulling reaction (1) to the right (as described above). This significantly decreases the sensor response time.

It was also found that there is no substantial difference in response for a matrix CA concentration of 0.09 mM and 0.5 mM for aqueous samples, but the higher carbonic anhydrase concentration [CA], did give a flatter response curve in whole blood. Furthermore, sensors with carbonic anhydrase and the standard urease matrix concentration in a cocktail of 0.07 mM, gave a similar response to sensors with carbonic anhydrase and 20% more urease. This is consistent with gains in linearity at the high end of the urea response curve and improved precision with the addition of the carbonic anhydrase (i) to limit the reverse reaction i.e. production of urea from $NH_4^+$ and $HCO_3^-$ and (ii) from the additional buffering capacity arising from the carbonate anion.

Kinetic studies of the BUN sensor indicate two different rate mechanisms are operative over the analyte range of 1-50 mM urea. At the high end of this range, the sensor response is limited by the concentration of urease, as is indicated in modeling studies after Carr & Bowers (1980) p. 209-210. At the low end it is substrate limited.

Where the object of the invention is to make single-use BUN sensors, i.e. ones that are used with a single blood sample and then discarded, as in the -i-STAT system, many millions of these sensors may be manufactured annually. In this example, addition of CA and buffer to the matrix may contribute to reduced lot-to-lot variability of manufacturing lots at the high end of the analyte range. The extent to which the urease enzyme concentration, as the limiting step is reduced, also may assist in better sensor performance.

It is desirable that the preferred embodiment of the improved BUN sensor incorporate the following features, (i) sodium phosphate buffer at pH 7.4 is best added to the latex mixture (BUN cocktail) that includes the enzymes as this considerably extends the shelf-life of the mixture, (ii) prior to addition to the mixture, the enzyme urease is best dialyzed against sodium phosphate buffer to increase the enzyme kinetics, and (iii) carbonic anhydrase is best added to the mixture to increase the efficiency of the urea conversion to $NH_4^+$. The following experimental data provide support for these conclusions.

The performance of the prior art BUN sensor and new BUN sensor are compared in the FIGS. 4-7. These figures show a portion of the BUN electrode response as a function of time. The portion of the response at time<14 s indicates the potentiometric response, with respect to the reference electrode, of the BUN electrode to the calibrant solution. The signal response at time>18 s is that of the BUN sensor to the test sample, which may be an aqueous-based, control material or a whole blood sample. The reference electrode is described in jointly owned U.S. Pat. No. 4,933,048, which is incorporated by reference herein. Other reference electrodes are well known in the electrochemical art could also be used with these BUN sensors.

Figure 4A:
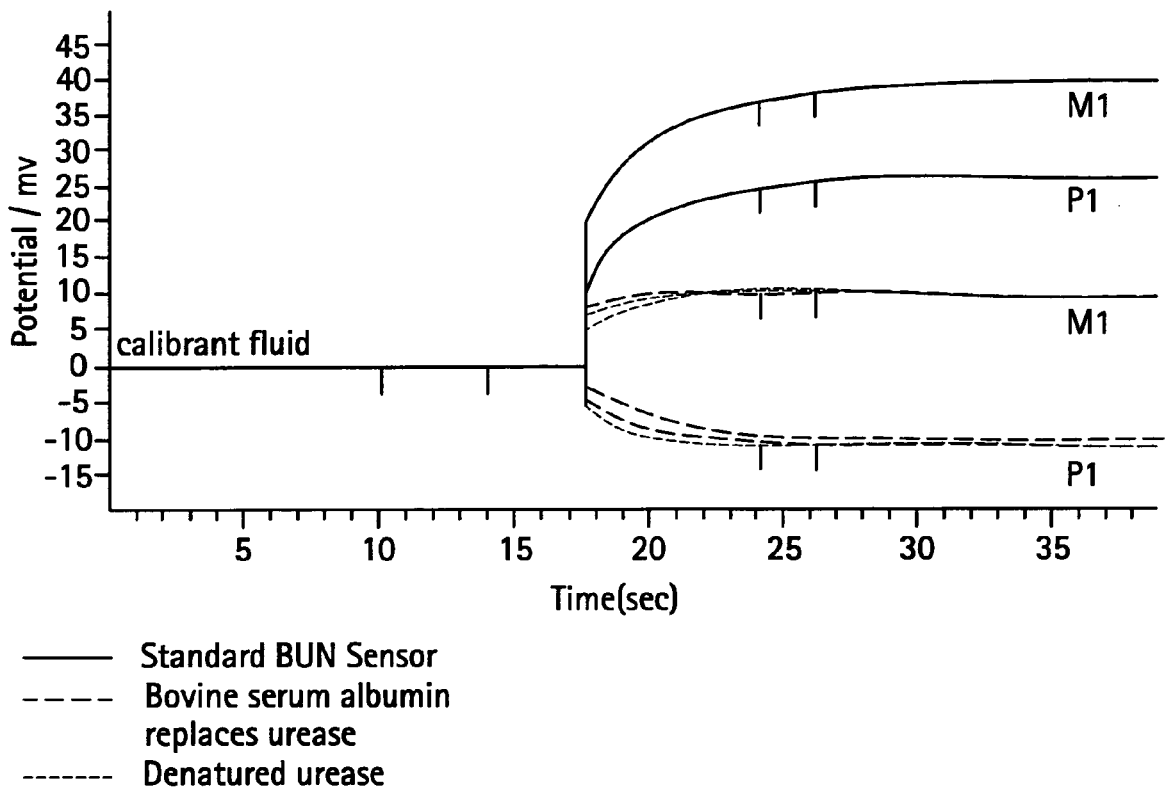

FIG. 4A shows the response curves to aqueous control materials using different BUN sensor compositions. The standard BUN sensor, based on -i-STAT prior art, is indicated by a solid black line. The long dash indicates a BUN sensor made with denatured urease. The short dash indicates a BUN sensor made with bovine serum albumin replacing the urease. This graph demonstrates that the signal is generated by the presence of urea being converted by urease enzyme.

Figure 4B:
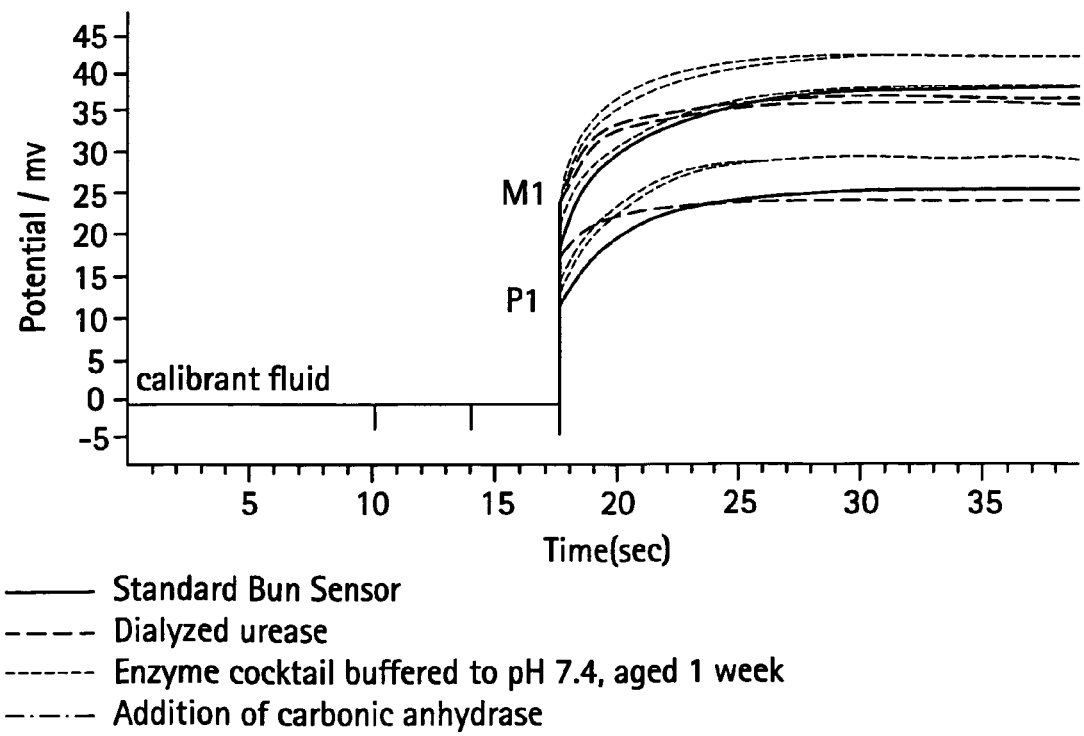

FIG. 4B shows performance indicated with a solid line for a standard BUN sensor. A short dash shows enzyme cocktail buffered to pH 7.4 and aged 1 week before being microdispensed. An intermediate dash indicates a BUN sensor which also includes carbonic anhydrase and the long dash indicates dialyzed urease. The presence of carbonic anhydrase exhibits an increased signal.

The long dash curve is the BUN cocktail prepared with urease dialyzed against 50 mM phosphate buffer. An important feature is the greater initial response after the transition from contact with calibrant fluid to a blood sample, suggesting that the urease kinetics are substantially increased, i.e. the urease enzyme activity is enhanced and effects the rapid conversion of urea to the product $NH_4^+$, and approaches the ideal "step function" response curve of theoretical potentiometric sensors.

Addition of carbonic anhydrase (CA) to the BUN cocktail the intermediate dash increases the amount of $NH_4^+$ converted from urea. In other words, CA increases the efficiency of the conversion of urea to ammonium ion. The implication here is that the sensitivity of the sensor increases with the addition of CA.

FIGS. 5-7 are plots from a shelf-life study with sensors stored at a constant 40° C. after manufacture. Storage at this elevated temperature provides a means for simulating an increased rate of degradation of sensors. This can provide a means for predicting the actual shelf-life of sensors stored under more typical conditions, e.g. room temperature and refrigeration. For manufactured sensors of the type described here, it is necessary to ensure that sensors remain usable for up to about one year after the purchase date. Response curves in whole blood and in aqueous fluid (m1) are shown for sensors stored at the elevated storage temperature for one (d1) and four (d4) days.

Two different manufactured sensor batches (A and B) were used for the standard condition. Only data for the carbonic anhydrase modifications (at two concentrations, 0.09 mM and 0.5 mM) are shown in FIG. 5.

The first plot shows the whole blood (wb) response (FIG. 5). The key features of the CA modification are (i) the increased mV response for a given change in urea concentration, i.e., more efficient conversion of urea to ammonium ion, and (ii) the "flattened" curve shape between about 25 and 40 s, implying improved steady-state operation. The [CA]=0.5 mM sensor appears to give a slightly flatter curve shape than the [CA]=0.09 mM sensor. Significantly, both CA sensors show negligible decline in potential between 25 and 40 s which is an improvement over the standard sensor design where CA is absent.

The sensor behavior after four days (d4) at 40° C. incubation is similar to that at one day (d1) as shown in FIG. 6. Note that the lower response compared to d1 is due to different wb samples. An ideal sample data-collection window (see disclosure of jointly owned U.S. Pat. No. 5,112,455) placement for the sensor with CA would be at approximately 30 s.

The aqueous fluid response for the BUN sensors at d1 in FIG. 7 is similar to those shown in FIG. 6. The sensor response to the m1 aqueous fluid after four days at 40° C. incubation is given below. The CA-containing sensor shows the same increased mV response as for the whole-blood samples. A comparison of the response curves at a 30 s data-collection window for the CA-containing sensor shows only a small difference between whole-blood and aqueous samples; this is a useful improvement over the difference observed between whole-blood and aqueous samples for the standard prior art sensor.

Data disclosed above show (i) that the prior art BUN sensor is enzyme-limited at high concentrations of urea, however significant improvements in sensor response can be achieved with the addition of carbonic anhydrase, (ii) stability of the enzyme matrix (Elvace) is related to the presence of acetic acid and that addition of a buffering component assists in extending its lifetime for sensor application, e.g. microdispensing, (iii) maintenance of an optimal pH in the BUN sensor is crucial to ensuring high urease activity and thus maximum BUN sensor performance and it can be achieved by adding buffer to the matrix, (vi) addition of carbonic anhydrase gives BUN sensors with minimal differences in the response curves between whole-blood and aqueous samples, and (v) addition of carbonic anhydrase to the matrix provides sensors with acceptable shelf-life.

The following sections (i) provide a description of the manufacture of the preferred embodiment of the new BUN sensor, (ii) disclose alternative matrix materials for UR and CA immobilization, (iii) give details on the biochemical properties and sources of UR and CA, (iv) disclose alternative membrane buffering systems to phosphate, and (v) disclose alternative ways of making UR-CA membranes for attachment to traditional electrodes, as the invention is not limited to microfabricated sensor applications.

Manufacture of a Preferred Embodiment of the New BUN Sensor

A preferred embodiment of the new BUN sensor is manufactured using a combination of thin-film microfabrication processes and microdispensing techniques. It comprises a thin film silver-silver chloride indicator electrode operating in combination with a thin-film silver-silver chloride reference electrode of the type described in U.S. Pat. No. 4,933,048.

A substrate wafer of silicon is overlaid with an insulating layer of silicon dioxide, prepared by thermal oxidation. Metal layers of titanium/tungsten, and then silver are deposited on the silicon dioxide base wafer, then patterned using photolithographic techniques. An electrically insulating layer such as polyimide polymer or additional silicon dioxide is then photo-patterned to isolate adjacent sensor circuitry. The silver-silver chloride indicator electrode (diameter ~200 microns) is prepared from the patterned silver using traditional techniques, e.g. electrochemical, chlorine gas plasma and oxidation of $Ag^0$ by an inorganic oxidant such as $Cr_2O_7^{2-}$ or $Fe^{3+}$ in the presence of chloride ion.

The remaining layers of the BUN electrode include two thick-film structures: (i) a semi-permeable membrane film, comprising an organic polymer layer (e.g., poly(vinyl chloride)—PVC), and an ammonium ion ionophore; and (ii) the outermost biolayer, comprising in this particular sensor, a film-forming latex (e.g., poly(vinyl acetate-co-vinyl alcohol)) and a sufficient amount of the enzymes urease and carbonic anhydrase. These layers are deposited by a microdispensing technique as described in jointly owned U.S. Pat. No. 5,554,339, which is incorporated by reference.

The reference electrode portion of the unit cell may be comprised of overlaid structures described in U.S. Pat. Nos. 4,933,048 and 5,200,051, both incorporated by reference.

The thick-film ammonium ion-sensitive structure comprises a poly(vinyl chloride) (PVC) binder, tris(2-ethylhexyl) phosphate as a plasticizer, and nonactin as the ionophore. The indicator electrode can be made selective for different ions by using the same binder and plasticizer composition but with different ionophores. For example, valinomycin, monensin and (methyl)monensin, and tridodecylammonium chloride have been used to make potassium, sodium, or chloride-ion selective electrodes, respectively. Other ionophores may include, but are not limited to crown ethers, trialkylamines, or phosphate esters, and the like. Alternatively, other polymeric binder materials may be used besides PVC. These polymers may include, for example, silicon rubber, polytetrafluoroethylene plastics, or derivatives of PVC containing ionizable functional groups (e.g., carboxylates). Other plasticizers suitable for use in the present invention may include, but are not limited to tris(2-ethylhexyl)phosphate, nitrocymene, 2-nitrophenyloctyl ether, dibutyl sebacate, diethyl adipate, phthalates, propylene carbonate, 5-phenylpentanol, or mixtures thereof. Still other binders and ionophore combinations may occur to those skilled in the art, which are within the scope of the present invention. The resulting semi-permeable ion-selective film may have a thickness in the range of about 2 microns to about 200 microns, preferably about 10 to about 30 microns.

At this point, it is important to distinguish between the properties of particle latices and their film-forming counterparts. A particle latex comprises a solid polymeric structure, such as polystyrene, which is coated with a hydrophilic material that allows the polymer particle to be waterborne. Particle latex materials have been used traditionally to immobilize all manner of biologically active materials including enzymes (See, Kraemer, D. et al., U.S. Pat. No. 4,710,525). Particle latexes coated with CA and UR may be used in the present invention.

By contrast, a film-forming latex is a colloidal solution comprised of a mobile polymeric liquid core, such as a vinyl acetate, with a hydrophilic outer coating. Such a film-forming latex is made by an emulsion-polymerization process in which a water-immiscible organic monomer or a mixture of monomers is added to an aqueous medium containing a free radical catalyst. The polymerization may be initiated, for example, by mechanical agitation (See, for example, Vanderhoff, J. W., J. Poly. Sci. Polymer Symposium 1985, 72, 161-198). When this material is dried the particles coalesce to form a film which cannot be redispersed in water. Because film-forming latices are water-based and contain both hydrophilic and hydrophobic components, one may speculate that these compositions are able to provide a stabilizing environment for biologically active species, e.g. enzymes including CA and UR, and constitute an effective medium for the immobilization or incorporation of the same.

It has further been found that film-forming latices from both natural and synthetic sources are of significant utility. For example, the following synthetic monomers, their chemically-modified analogues, copolymers, or mixtures thereof may be used to make a film-forming latex: vinyl acetate, ethylene, acrylate or acrylic acid, styrene, or butadiene. These and many other materials known to those skilled in the art are available commercially from many sources including Reichhold, Air Products, DuPont, Dow Chemical, or Imperial Chemical Company. Natural isoprene-based polymers are also useful and available from Imperial Adhesives and Chemicals, Inc. and from General Latex and Chemical Corp. Elvace from Reichhold is used in the preferred embodiment of the BUN sensor.

Moreover, these materials retain their film-forming properties even when non-latex water-soluble components (e.g., proteins, enzymes, polysaccharides, and hydrocolloids such as agarose, locust bean gum, guar gum, or combinations of hydrocolloids, or synthetic polymers such as poly(vinyl alcohol), poly(vinyl pyrrolidone), polyacrylamide and the like) comprise up to about 25% by weight of the solids content. In this respect, a significant consideration related to a microfabrication process for the production of sensors is that the established film adheres effectively to a planar substrate even in the presence of large amounts of additives (i.e., enzymes).

Various methods can be used to define a layer on a planar substrate. If a thick layer (about 5 to about 200 microns) is required, microdispensing of a viscous film-forming latex composition (<500 Centipoise as measured on a Brookefield RV viscometer) is preferred. However, if a thin layer (about 0.2 to less than about 5 microns) is required, a composition with a lower viscosity is used which can be microdispensed directly onto the indicator electrode, or alternatively, either microdispensed or spin-coated onto a positive resist layer (e.g., Shipley AZ 1370 SF) which has been patterned to leave the area over the indicator electrode exposed. Any suitable solvent known in the art, such as n-butylacetate and the like, is then used to lift off the resist, along with the excess latex. A separate technique using a photoresist cap may also be used.

Control of the surface energy may be used beneficially to control the spreading of the microdispensed reagent (and, thus, its dimensionality, such as thickness). A fluorocarbon e.g., carbon tetrafluoride, plasma treatment of a polyimide layer surrounding the indicator electrode causes the aqueous based latex to exhibit a high contact angle (i.e., minimizes spreading and increasing thickness).

To immobilize one or more biologically active species in a latex layer it is possible either to mix the species with the latex prior to deposition or impregnate the layer after deposition. Stability of the biologically active species, particularly enzymes, can be enhanced by adding a cross-linking agent either before or after deposition. These cross-linking agents are well-known in the art and may include such compounds as glyoxal, glutaraldehyde, melamine formaldehyde, urea formaldehyde, and phenol formaldehyde. Other suitable cross-linking agents may possess at least two functional groups which may include vinyl, carboxyl, anhydride, amine, amide, epoxy, hydroxyl, cyano, isocyanato, thiol, halo, in addition to formyl, and stable combinations of these functional groups (e.g., a chloroalkylepoxide). These additives can significantly enhance the wet-strength of the biolayer and extend the shelf-life of the completed sensor. In almost all instances, one or more of the biologically active macromolecules listed in the preceding or following sections of this disclosure may be successfully immobilized using a film-forming latex such as Elvace or Elmer's Glue.

The porosity of the enzyme matrix can be controlled to a significant extent by incorporating certain additives, such as salts (e.g., sodium chloride) or sugar alcohols (e.g., mannitol, erythritol, or sorbitol), into the latex mixture prior to deposition. For example, the addition of sorbitol to the latex formulation (at about 1 g/dL of solution) significantly decreases the time needed for wet-up of a desiccated urea sensor. A shorter wet-up period (see jointly owned U.S. Pat. No. 5,112,455) provides, in turn, for a faster response.

In the preferred embodiment, the new BUN sensor is packaged into a cartridge of the type disclosed in U.S. Pat. No. 5,096,669, which also contains a calibrant solution. It is contained in a calibrant package (CALPAK), which is ruptured during the blood sample analysis. The typical sequence of events includes the CALPAK being ruptured and then the calibration solution passing over the sensor and wetting up the sensor. Typically, the CALPAK of prior art cartridges contained the following ions, sodium, potassium, calcium, chloride, bicarbonate and also HEPES buffer, glucose, lactate, urea, creatine and creatinine.

With regard to urea in the CALPACK, as it was discovered that this substrate can create a build up of product, which causes feedback inhibition of the enzyme, it can be removed from the calibration fluid, thereby removing feedback inhibition of the enzyme. The preferred constitution of the CALPAK for the new BUN sensor should include sodium, potassium, calcium, chloride, ammonium, bicarbonate, HEPES buffer, glucose, lactate, creatine and creatinine. In this embodiment ammonium ions rather than urea calibrate the BUN sensor.

Properties and Sources of Urease (E.C. 3.5.1.5)

An ideal property of urease for this application is that it has a low residual level of associated substrate (urea<0.0002 μmol/enzyme unit) and other nitrogenous compounds. Furthermore it should be free of contaminating proteases. Specific activities greater than 700 U/mg protein at 25° C. are ideal characteristics. The enzyme preparations should also be of high purity. Other desirable characteristics of urease are that the $K_m$ of the enzyme be in the range of 1 to 50 (mM), preferably closer to 50 mM and that the $V_{max}$ be greater than 16,000 (micromol/ml/min) and also the $K_{cat}$ be $5 \times 10^5$ min$^{-1}$ or greater.

In the preferred embodiment, the preferred source of urease is Jack Bean urease (E.C. 3.5.1.5) is Genzyme Diagnostics (One Kendall Square, Cambridge, Mass., USA, 02139). Item number 70-1661-01 ($K_m$: 9.39 mM; $V_{max}$: 16187 micromol/ml/min; $K_{cat}$: $5.91 \times 10^5$ min$^{-1}$) Other source of Jack Bean Urease (E.C. 3.5.1.5) include; (i) Sigma-Aldrich Canada Ltd. (2149 Winston Park Drive, Oakville, Ontario, Canada, L6H 6J8) Catalog number U1500, (ii) Toyobo (Toyobo Building, 17-9, Nihonbashi, Koami-cho, Chuo-ku, Tokyo, 103-8530, Japan) Catalog numbers URH-201 or URH-301 and (iii) Worthington Biochemical Corporation (730 Vassar Ave, Lakewood, N.J., USA, 08701)

Urease enzymes are also available from the following organisms; *Deinococcus radiodurans, Pseudomonas syringae* (pv. tomato), *Streptomyces avermitilis, Streptomyces coelicolor, Sulfolobus tokodaii, Brucella melitensis, Brucella suis, Alcaligenes eutrophus* (*Ralstonia eutropha*), *Actinobacillus pleuropneumoniae* (*Haemophilus pleuropneumoniae*), *Bacillus pasteurii, Bacillus* sp. (strain TB-90), *Bacillus subtilis, Bordetella bronchiseptica* (*Alcaligenes bronchisepticus*), *Clostridium perfringens, Escherichia coli, Haemophilus influenzae, Klebsiella aerogenes, Lactobacillus fermentum, Listonella damsela* (*Vibrio damsela*), *Morganella morganii* (*Proteus morganii*), *Mycobacterium tuberculosis, Mycobacterium bovis, Proteus mirabilis, Proteus vulgaris, Rhizobium meliloti* (*Sinorhizobium meliloti*), *Staphylococcus aureus* (strain Mu50/ATCC 700699), *Staphylococcus aureus* (strain N315), *Staphylococcus aureus* (strain MW2), *Staphylococcus epidermidis, Staphylococcus xylosus, Streptococcus salivarius, Synechocystis* sp. (strain PCC 6803), *Ureaplasma parvum* (*Ureaplasma urealyticum* biotype 1), *Ureaplasma urealyticum* (*Ureaplasma urealyticum* biotype 2), *Yersinia enterocolitica, Yersinia pestis, Yersinia pseudotuberculosis, Actinobacillus pleuropneumoniae* (*Haemophilus pleuropneumoniae*), *Bacillus pasteurii, Bacillus* sp. (strain TB-90), *Bacillus subtilis, Bordetella bronchiseptica* (*Alcaligenes bronchisepticus*), *Bordetella parapertussis, Clostridium perfingens, Haemophilus influenzae, Helicobacter felis, Helicobacter heilmannii, Helicobacter mustelae, Helicobacter pylori* (*Campylobacter pylori*), *Helicobacter pylori* J99 (*Campylobacter pylori* J99), *Klebsiella aerogenes, Lactobacillus fermentum, Morganella morganii* (*Proteus morganii*), *Mycobacterium tuberculosis, Mycobacterium bovis, Proteus mirabilis, Proteus vulgaris, Rhizobium meliloti* (*Sinorhizobium meliloti*), *Staphylococcus aureus* (strain Mu50/ATCC 700699), *Staphylococcus aureus* (strain N315), *Staphylococcus aureus* (strain MW2), *Staphylococcus epidermidis, Staphylococcus xylosus, Streptococcus salivarius, Synechocystis* sp. (strain PCC 6803), *Ureaplasma parvum* (*Ureaplasma urealyticum* biotype 1), *Ureaplasma urealyticum* (*Ureaplasma urealyticum* biotype 2), *Yersinia enterocolitica, Yersinia pestis, Yersinia pseudotuberculosis, Actinomyces naeslundii, Actinobacillus pleuropneumoniae* (*Haemophilus pleuropneumoniae*), *Agrobacterium tumefaciens* (strain C58/ATCC 33970), *Alcaligenes eutrophus* (*Ralstonia eutropha*), *Anabaena* sp. (strain PCC 7120), *Bacillus halodurans, Bacillus pasteurii, Bacillus* sp. (strain TB-90), *Bacillus subtilis, Bordetella bronchiseptica* (*Alcaligenes bronchisepticus*), *Bordetella parapertussis, Bordetella pertussis, Bradyrhizobium japonicum, Brucella abortus, Candidatus Blochmannia floridanus, Clostridium perfringens, Corynebacterium efficiens, Corynebacterium glutamicum*

(*Brevibacterium flavum*), *Escherichia coli* O157:H7, *Escherichia coli*, *Haemophilus influenzae*, *Klebsiella aerogenes*, *Klebsiella pneumoniae*, *Lactobacillus fermentum*, *Morganella morganii* (*Proteus morganii*), *Mycobacterium tuberculosis*, *Mycobacterium bovis*, *Proteus mirabilis*, *Prochlorococcus marinus* (strain MIT 9313), *Prochlorococcus marinus* subsp. *pastoris* (strain CCMP 1378/MED4), *Prochlorococcus* sp. (strain PCC 9511), *Proteus vulgaris*, *Pseudomonas aeruginosa*, *Pseudomonas putida* (strain KT2440), *Pseudomonas syringae* (pv. tomato), *Ralstonia solanacearum* (*Pseudomonas solanacearum*), *Rhizobium loti* (*Mesorhizobium loti*), *Rhizobium leguminosarum* (biovar viciae), *Rhizobium meliloti* (*Sinorhizobium meliloti*), *Rhodobacter capsulatus* (*Rhodopseudomonas capsulata*), *Rhodobacter sphaeroides* (*Rhodopseudomonas sphaeroides*), *Staphylococcus aureus* (strain Mu50/ATCC 700699), *Staphylococcus aureus* (strain N315), *Staphylococcus aureus* (strain MW2), *Staphylococcus epidermidis*, *Staphylococcus xylosus*, *Streptomyces avermitilis*, *Streptomyces coelicolor*, *Streptococcus salivarius*, *Streptococcus thermophilus*, *Synechococcus elongatus* (*Thermosynechococcus elongatus*), *Synechococcus* sp. (strain WH7805), *Synechococcus* sp. (strain WH8102), *Synechocystis* sp. (strain PCC 6803), *Ureaplasma parvum* (*Ureaplasma urealyticum* biotype 1), *Ureaplasma urealyticum* (*Ureaplasma urealyticum* biotype 2), *Vibrio parahaemolyticus*, *Yersinia enterocolitica*, *Yersinia pestis*, *Yersinia pseudotuberculosis*, *Canavalia ensiformis* (Jack bean) (Horse bean), *Cryptococcus neoformans* (*Filobasidiella neoformans*), *Helicobacter bizzozeronii*, *Helicobacter felis*, *Helicobacter heilmannii*, *Helicobacter hepaticus*, *Helicobacter mustelae*, *Helicobacter pylori* J99 (*Campylobacter pylori* J99), *Helicobacter pylori* (*Campylobacter pylori*), *Schizosaccharomyces pombe* (Fission yeast), *Glycine max* (Soybean).

These enzymes can be purified from their natural sources or from gene fragments cloned from these organisms and overexpressed in recombinant clones. Additional information on urease enzymes is updated on the web site www.expasy.ch or the NCBI databases.

Properties and Sources of Carbonic Anhydrase (E.C. 4.2.1.1)

An ideal property of Carbonic Anhydrase for this application is that it has low residual levels of nitrogenous compounds and be free of contaminating proteases. Specific activity greater than 2500 Wilbur-Anderson units/mg protein at 0° C. is quoted by the vendor. (Wilbur, K. M. and N. G. Anderson, 1948, Journal of Biological Chemistry, 176: 147-154) The enzyme preparations should be of high purity.

Other ideal characteristics of Carbonic Anhydrase are a $K_m$ value between 1 to 50 mM, $V_{max}$ greater than 50 (microl/ml/min), with an ideal level above 10,000 and a $K_{cat}$ value greater than 75, but with an ideal level of greater than $10^5$ min$^{-1}$.

In the preferred embodiment, the preferred source is bovine Carbonic Anhydrase (E.C. 4.2.1.1) from Sigma-Aldrich Canada Ltd. (2149 Winston Park Drive, Oakville, Ontario, Canada, L6H 6J8) Catalog number C3934. ($K_m$: 1.31 mM; $V_{max}$: −64.4 micromol/ml/min; $K_{cat}$: 76.24 min$^{-1}$). Another source of Bovine Carbonic Anhydrase (E.C. 4.2.1.1) is Worthington Biochemical Corporation (730 Vassar Ave, Lakewood, N.J., USA, 08701).

Carbonic Anhydrase enzymes are also available from the following organisms: *Caenorhabditis elegans*, *Chlamydomonas reinhardtii*, *Flayeria linearis*, *Equus caballus* (Horse), *Macaca mulatta* (Rhesus macaque), *Macaca nemestrina* (Pig-tailed macaque) *Monodelphis domestica* (Short-tailed grey opossum), *Arabidopsis thaliana* (Mouse-ear cress), *Bos taurus* (Bovine), *Gallus gallus* (Chicken), *Flayeria linearis*, *Tribolodon hakonensis* (Japanese dace), *Equus caballus* (Horse), *Rattus norvegicus* (Rat), *Caenorhabditis elegans*, *Bos taurus* (Bovine), *Ovis aries* (Sheep), *Arabidopsis thaliana* (Mouse-ear cress), *Hordeum vulgare* (Barley), *Pisum sativum* (Garden pea), *Spinacia oleracea* (Spinach), *Nicotiana tabacum* (Common tobacco), *Arabidopsis thaliana* (Mouse-ear cress), *Hordeum vulgare* (Barley), *Pisum sativum* (Garden pea), *Oryctolagus cuniculus* (Rabbit), *Spinacia oleracea* (Spinach), *Nicotiana tabacum* (Common tobacco), *Homo sapiens* (Human), *Mus musculus* (Mouse), Vaccinia virus (strain Copenhagen), Vaccinia virus (strain WR), Variola virus, *Flayeria bidentis*, *Flayeria brownii*, *Flayeria pringlei*, *Brachydanio rerio* (Zebrafish) (*Danio rerio*), *Anabaena* sp. (strain PCC 7120), *Dunaliella salina*, *Erwinia carotovora*, *Klebsiella pneumoniae*, *Methanosarcina thermophila*, *Neisseria gonorrhoeae*, *Escherichia coli*, *Escherichia coli* O157:H7, *Helicobacter pylori* J99 (*Campylobacter pylori* J99), *Helicobacter pylori* (*Campylobacter pylori*), *Synechococcus* sp. (strain PCC 7942) (*Anacystis nidulans* R2), *Synechocystis* sp. (strain PCC 6803), *Caenorhabditis elegans*, *Arabidopsis thaliana* (Mouse-ear cress), *Medicago sativa* (Alfalfa), *Synechococcus* sp. *Zea mays* (Maize), *Urochloa panicoides* (Panic liverseed grass), *Porphyridium purpureum*, a panicoides (Panic liverseed grass), *Mycobacterium bovis*, *Synechococcus* sp. (strain WH8102), *Rhodopirellula baltica*, *Bacillus cereus* (strain ATCC 14579/DSM 31), *Nitrosomonas europaea*, *Phaseolus vulgaris* (Kidney bean) (French bean), *Lotus japonicus*, *Flayeria bidentis*, *Leptospira interrogans*, *eutrophus* (*Ralstonia eutropha*), *Arabidopsis thaliana* (Mouse-ear cress), *Gossypium hirsutum* (Upland cotton), *Riftia pachyptila* (Tube worm), *Corynebacterium glutamicum* (*Brevibacterium flavum*), *Methanosarcina mazei* (*Methanosarcina frisia*), *Nicotiana tabacum* (Common tobacco), *Brucella melitensis*, *Salmonella typhimurium* Q92KYO, *Rhizobium meliloti* (*Sinorhizobium meliloti*) [Plasmid pSymA (megaplasmid 1)], *Coccomyxa* sp. PA *Bacillus halodurans*, *Gossypium hirsutum* (Upland cotton), *Solanum tuberosum* (Potato) [Chloroplast], *Drosophila melanogaster* (Fruit fly), *Streptomyces coelicolor*, *Rhodopseudomonas palustris*, *Gossypium hirsutum* (Upland cotton), *Glycine max* (Soybean), *Phaseolus aureus* (Mung bean) (*Vigna radiata*), *Anthopleura elegantissima* (Sea anemone).

These enzymes can be purified from their natural sources or from gene fragments cloned from these organisms and overexpressed in recombinant clones. Additional information on carbonic anhydrase enzymes is updated on the web site www.expasy.ch or the NCBI databases.

Buffering System for Enzyme Matrix

From the literature, the pH optimum for urease is reported as pH 8.0. (Wall & Laidler, 1953, The Molecular Kinetics of the Urea-Urease System. IV. The Reaction in an Inert Buffer, Archives of Biochemistry and Biophysics, vol 43: 307-311). Our data suggest that a pH less than pH 8.0, closer to pH range of 6.5 to 7.4, for our urease preparation gives an optimal enzyme activity.

Preferred buffer for use in the preferred cartridge device is −100 mM sodium phosphate at pH −6.8. Sodium phosphate buffers ranging from 10 to −200 mM can be used in the preferred embodiment, including said buffers in the pH range from about −6.5 to 7.4.

Other buffers useful in this device include potassium phosphate, TRIS (trishydroxymethylaminomethane), e.g. TRIS-$H_2SO_4$ (Wall & Laidler, 1953), HEPES (Cesareo & Langton, 1992, Kinetic Properties of *Helicobacter pylori* urease compared with jack bean urease, FEMS Microbiology Letters, vol 99: 15-22), TRIS-HCl buffer and barbitone.

Other buffers not generally recommended for use with urease are those that include sulfite, bisulfite and phenylsulfite ions. (G. Fasman & C. Niemann, 1951, A reinvestigation of the kinetics of the Urease-Catalyzed hydrolysis of Urea. I. The activity of urease in the presence of Sodium and Potassium Phosphate, Journal of the American Chemical Society, vol 73: 1646-1650.)

Membranes with Urease and Carbonic Anhydrase for Use in Non-microfabricated Devices The present invention is not limited to sensing devices that are microfabricated. Traditionally, sensing electrodes are made from glass structures with membranes held in place over the tip of the structure by means of an O-ring or similar fastening component, e.g. a fixture incorporating an attached membrane where the fixture is capable of mating with an electrode so as to abut the membrane to the ion-selective electrode surface. The prior art for glass potentiometric urea sensors is well known and can employ a second, ion-selective electrode (ISE) in conjunction with the enzyme layer to detect either ammonium ions, via a nonactin-based ISE, or hydronium ions, via pH ISE. Membranes that contain urease and that can be attached to a glass electrode by means of an O-ring are well known in the art. Similar membranes are also well known for enzymes such as glucose oxidase, as in the Yellow Springs Instruments glucose analyzer. It is well known that instruments of this kind have re-usable electrodes where the membrane is exposed to a series of samples and gives a sample urea concentration value for each. Intermittently or with each sample the membrane is also exposed to one or more calibrant fluids. Typically a wash fluid is also applied to the membrane between samples.

In the present invention membranes that contain both urease and carbonic anhydrase enzymes may be prepared. This immobilization may be either by covalent attachment or physical entrapment, in a polymeric media. Such polymeric materials include but are not limited to nitrocellulose (as described in U.S. Pat. No. 4,713,165); poly (vinyl alcohol), and copolymers of poly (vinyl alcohol), polypyrrole, polyvinyl pyridine, polyalkylthiophenes (as described in U.S. Pat. No. 5,858,186) and polyurethane (as described in U.S. Pat. No. 6,673,565).

The urease and carbonic anhydrase enzymes may also be immobilized, either by covalent attachment or physical entrapment, in a sol-gel, or bovine serum albumin (BSA) cross-linked with glutaraldehyde (as in U.S. Pat. No. 4,927, 516). Alternatively, immobilization may be based on antibodies that bind urease and carbonic anhydrase.

The preferred embodiment is a polyurethane membrane prepared as follows: (i) mix pH 7.8 Tris buffer (10 mM) and surfactant (e.g. Pluronic F-68) in a vessel, (ii) add urease and carbonic anhydrase solutions made in the same buffer, (iii) add Hypol™ isocyanate functionalism polyurethane prepolymer (Hampshire Chemical Corp., a subsidiary of Dow Chemical) and thoroughly mix, (iv) inject mixture into a membrane mold, and (v) cure membrane and cut into disks for attachment to an ammonium ion-selective electrode.

An alternative embodiment in which urease and carbonic anhydrase are immobilized in bovine serum albumin (BSA) cross-linked with glutaraldehyde is also provided. A urease and carbonic anhydrase layer is deposited to a thickness of about 1 mm on the surface of an ammonium ion-selective electrode. The enzyme layer is deposited by a cross-linking process using glutaraldehyde as a cross-linking agent. The cross-linked structure prevents the urease and carbonic anhydrase from eluting into a liquid specimen. (Solution A): 15 wt-% bovine serum albumin was dissolved in a pH 8.0 phosphate buffer solution, and 1.5 g of urease and 0.2 g of carbonic anhydrase was dissolved in 5 mL of the resulting solution. (Solution B): 25% glutaraldehyde aqueous solution. (Solution C): 10% glycine aqueous solution. A wire electrode is dipped into Solution A, dried for about 1 min, dipped into Solution B and then dried for 1 min. This procedure was repeated until a layer having a thickness of about 1 mm was formed on the electrode. The electrode was then dipped into Solution C for 1 min, thereby removing unreacted enzyme. This completes the deposition of the urease and carbonic anhydrase layer.

Membranes of the type described here may be attached to any class of sensor known in the art including potentiometric sensors, amperometric sensors, conductimetric sensors, optical sensors, e.g. fiber optic and wave guide devices, piezoelectric sensor, acoustic wave sensors and the like. Likewise the combination of urease and carbonic anhydrase can be immobilized directly onto these sensors by means of chemical cross-linking reagents or by physical adsorption. The optical sensor may include a dye material that changes optical properties as a function of concentration of $H^+$, $NH_4^+$, $CO_2$ and $HCO_3^-$.

Additional BUN Sensors

A potentiometric chemical sensor for urea can be viewed as a system, which is constructed from functionally dissimilar components. In one embodiment of the blood urea nitrogen (BUN) sensor, the outermost layer, the one in contact with the analyte solution, permits the transport of urea while also serving to immobilize the enzymes urease and carbonic anhydrase. These enzymes catalyze the hydrolysis of urea to ammonia as described above. At neutral pH values, the ammonia thus produced exists predominantly as ammonium ions. By interposing a separate layered structure, which contains an ionophore with high sensitivity and selectivity for ammonium ions between the enzyme containing layer and a silver-silver chloride indicator electrode, the ammonium ion concentration at the electrode interface can be measured. In this type of measurement, the potential difference between the indicator electrode and a reference electrode is recorded.

The analytical value of the measurement is derived from the fact that the magnitude of the potential difference is related by the Nicolsky equation (Eq. 3, below) to the concentration of the analyte, in this case, urea:

$$E=E_o+RT/nF \log [A+\Sigma(a,b)k(a,b)B] \qquad (3)$$

where E is the measured electromotive force (signal), R is the gas law constant, T is the absolute temperature, n is the absolute value of the charge on analyte species a (e.g., n=1 for the ammonium ion), F is the Faraday constant, A is the activity of the analyte species a, B is the activity of an interfering chemical species b, $k_{a,b}$ is the interference coefficient associated with the effect of the presence of chemical species b on the electrochemical potentiometric determination of the activity of the analyte species a, and $E_o$ is a constant independent of T, A, or B. For additional discussion of the Nicolsky equation, refer to Amman, D., *Ion-Selective Microelectrodes*, Springer, Berlin (1986) p. 68 and references cited therein.

In a preferred embodiment of the present invention, the unit cell for the BUN sensor comprises a thin film silver-silver chloride indicator electrode operating in combination with a thin-film silver-silver chloride reference electrode.

Referring now to the topological illustration in FIG. 8, the substrate wafer, 20, is silicon, with an overlaid insulating layer of silicon dioxide, 15. The first metal layer, 10, is titanium and serves the functions of a conductor and an adhesion layer to the wafer. Succeeding layers 4 and 4', are the silver and silver chloride layers. On the left side of FIG. 8, the remaining layers of the indicator electrode include (i) a semi-permeable membrane film, 25, comprising an organic polymer layer (e.g., poly(vinyl chloride)—PVC) and an ammonium ion ionophore; and (ii) the outermost biolayer, 11, comprising in this particular sensor, a film-forming latex (e.g., poly(vinyl acetate-co-vinyl alcohol)) and a sufficient amount of the enzymes urease and carbonic anhydrase.

The reference electrode portion of the unit cell may be comprised of overlaid structures as shown in FIG. 8. In this particular embodiment, the metal and chloridized layers of the reference electrode are covered by an electrolyte layer, 12, which may comprise any material which is able to hold a high concentration of salt but which is, preferably, photoformable. In this respect, a polyvinylalcohol (PVA) formulation is the preferred material and may first be photopatterned and forms a water-permeable matrix that can subsequently be saturated with a salt, such as potassium chloride. A separate gas permeable membrane, 8', may also be present which serves to diminish the loss of electrolyte or salt to the bulk analytical sample but allows the rapid wet-up (i.e., passage of $H_2O$ or other small gaseous molecules) of the reference electrode prior to commencing the sample analysis. The photoresist cap 9, which may be a remnant of the patterning process need not be removed if it does not bar the free passage of solvent, solute, or ions. In a preferred embodiment, the reference electrode structure described in U.S. Pat. No. 4,933,048, incorporated herein by reference, is used. Alternatively, a reference electrode structure can be used in which the distance between the liquid junction and the surface of the silver/silver chloride is sufficiently large, such that the concentration of electrolyte in the immediate vicinity of the Ag/AgCl structure is substantially constant for a period of time sufficient to perform a measurement of the potential difference between the indicator electrode and the reference electrode.

As illustrated in FIG. 8, superimposed over the indicator electrode of a BUN sensor is a thick film ammonium ion-sensitive structure comprising a poly(vinyl chloride) (PVC) binder, tris(2-ethylhexyl)phosphate as a plasticizer, and nonactin as the ionophore. The indicator electrode can be made selective for different ions by using the same binder and plasticizer composition but with different ionophores. For example, valinomycin, monensin and (methyl)monensin, or tridodecylammonium chloride have been used to make potassium, sodium, or chloride-ion selective electrodes, respectively. Other ionophores may include, but are not limited to crown ethers, trialkylamines, or phosphate esters, and the like. Alternatively, other polymeric binder materials may be used besides PVC. These polymers may include, for example, silicon rubber, polytetrafluoroethylene plastics, or derivatives of PVC containing ionizable functional groups (e.g., carboxylates). Other plasticizers suitable for use in the present invention may include, but are not limited to tris(2-ethylhexyl)phosphate, nitrocymene, 2-nitrophenyloctyl ether, dibutyl sebacate, diethyl adipate, phthalates, propylene carbonate, 5-phenylpentanol, or mixtures thereof. Still other binders and ionophore combinations may occur to those skilled in the art, which are within the scope of the present invention. The resulting semi-permeable ion-selective film may have a thickness in the range of about 2 .mu.m to about 200 .mu.m, preferably about 10 to about 30 .mu.m.

Referring now to FIG. 9, indicator electrode, 30, and the adjacent reference electrode, 35, are each connected by an overpassivated signal line, 2, to a contact pad, 1. The unit cell is confined within a rectangular area, which is repeated in an array several hundred times on a single silicon wafer. In particular embodiments of the instant invention, other indicator electrodes may be present in the unit cell for the simultaneous measurement of other species (e.g., $Na^+$, $K^+$, or $Cl^-$) in addition to ammonium ion.

BUN Biolayer

At this point, it is important to distinguish between the properties of particle latices and their film-forming counterparts. A particle latex comprises a solid polymeric structure, such as polystyrene, which is coated with a hydrophilic material that allows the polymer particle to be waterborn. Particle latex materials have been used traditionally to immobilize all manner of biologically active materials (See, Kraemer, D. et al., U.S. Pat. No. 4,710,825). However, an important property of some but not all particle latices, which is unsuitable in the present application, is that even after these materials have been dried, the particles can be redispersed easily in water. By contrast, a film-forming latex is a colloidal solution comprised of a mobile polymeric liquid core, such as a vinyl acetate, with a hydrophilic outer coating. Such a film-forming latex is made by an emulsion-polymerization process in which a water-immiscible organic monomer or a mixture of monomers is added to an aqueous medium containing a free radical catalyst. The polymerization may be initiated, for example, by mechanical agitation (See, for example, Vanderhoff, J. W., J. Poly. Sci. Polymer Symposium 1985, 72, 161-198). When this material is dried the particles coalesce to form a film, which cannot be redispersed in water. Because film-forming latices are water-based and contain both hydrophilic and hydrophobic components, one may speculate that these compositions are able to provide a stabilizing environment for biologically active species and constitute an effective medium for the immobilization or incorporation of same.

It has further been found that film-forming latices from both natural and synthetic sources are of significant utility. For example, the following synthetic monomers, their chemically-modified analogues, copolymers, or mixtures thereof may be used to make a film-forming latex: vinyl acetate, ethylene, acrylate or acrylic acid, styrene, or butadiene. These and many other materials known to those skilled in the art are available commercially from many sources including Reichhold, Air Products, DuPont, Dow Chemical, or Imperial Chemical Company. Natural isoprene-based polymers are also useful and available from Imperial Adhesives and Chemicals, Inc. and from General Latex and Chemical Corp.

Moreover, these materials retain their film-forming properties even when non-latex water-soluble components (e.g., proteins, enzymes, polysaccharides such as agarose, or synthetic polymers such as poly(vinyl alcohol), poly(vinyl pyrrolidone), and the like) comprise up to about 25% by weight of the solids content. In this respect, a significant consideration related to a microfabrication process for the production of biosensors is that the established film adheres effectively to a planar substrate even in the presence of large amounts of additives (i.e., enzymes).

Various methods can be used to define a layer on a planar substrate. If a thick layer (about 5 to about 200 .mu.m) is required, microdispensing of a viscous film-forming latex composition (<500 Centipoise as measured on a Brookefield RV viscometer) is preferred. However, if a thin layer (about 0.2 to less than about 5 .mu.m) is required, a composition with a lower viscosity is used which can be microdispensed directly onto the indicator electrode, or alternatively, either microdispensed or spin-coated onto a positive resist layer (e.g., Shipley AZ 1370 SF) which has been patterned to leave the area over the indicator electrode exposed. Any suitable solvent known in the art, such as n-butylacetate and the like, is then used to lift off the resist, along with the excess latex. A separate technique using a photoresist cap may also be used.

Control of the surface energy may be used beneficially to control the spreading of the microdispensed reagent, and thus its dimensionality, such as thickness. A fluorocarbon (e.g., $CF_4$) plasma treatment of a polyimide layer surrounding the indicator electrode causes the aqueous based latex to exhibit a high contact angle (i.e., minimizes spreading and maximizing thickness).

To immobilize one or more biologically active species in a latex layer it is possible either to mix the species with the latex prior to deposition or impregnate the layer after deposition. The stability of the biologically active species, particularly enzymes, is usually enhanced by adding a crosslinking agent either before or after deposition. These crosslinking agents are well-known in the art and may include such compounds as glyoxal, glutaraldehyde, melamine formaldehyde, urea formaldehyde, and phenol formaldehyde. Other suitable crosslinking agents may possess at least two functional groups, which may include vinyl, carboxyl, anhydride, amine, amide, epoxy, hydroxyl, cyano, isocyanato, thio, halo, in addition to formyl, and stable combinations of these functional groups (e.g., a chloroalkylepoxide). These additives can often significantly enhance the wet-strength of the biolayer and extend the shelf-life of the completed sensor.

In a particular embodiment of the present invention, a film-forming latex is used to immobilize the enzymes urease and carbonic anhydrase. A higher enzymatic activity is achieved in this case compared to a urea sensor containing urease alone.

The porosity of the enzyme layer (biolayer) can be controlled to a significant extent by incorporating certain additives, such as salts (e.g., sodium chloride) or sugar alcohols (e.g., mannitol, erythritol, or sorbitol), into the latex mixture prior to deposition. For example, the addition of sorbitol to the latex formulation (1 g/dL of solution) significantly decreases the time needed for wet-up of the desiccated urea sensor. A shorter wet-up period provides that can give results for blood analyses more rapidly. To manufacture the base sensor, a silicon wafer with a topical layer of silicon dioxide, which had previously been cleaned, scrupulously with a mixture of concentrated sulfuric acid and hydrogen peroxide is placed into a plasma deposition system and layers of titanium (0.1 mu.m) and silver (0.5 .mu.m) are sputtered consecutively onto the wafer surface. The silver-titanium bilayer is then processed to localize it to a region, which in the final device acts as the ammonium ion sensor. This process is achieved by a standard lithographic technique in which the wafer is spin-coated with positive resist (Shipley AZ 1370 SF). After UV exposure of the photoresist through a mask and development (Shipley AZ 351), the exposed silver is removed by an aqueous solution of ferric nitrate (0.9 mM) as the etchant. The underlying titanium layer is then processed by means of the same photolithographic steps, but using an aqueous mixture of nitric acid (3.9M) and hydrofluoric acid (0.78M) is used as the etchant. N-methylpyrrolidone solvent is then used to remove the remaining photoresist to expose the required silver structures (diameter about 150 .mu.m).

To passivate the signal lines a photo-definable polyimide (DuPont 2703) is spin-coated onto the wafer. Once the wafer is UV exposed and developed with a solvent the polymer is baked in an oven at 350.degree. C. for 30 minutes under an inert atmosphere and left to cool to 150.degree. C. before removal.

The silver is then chloridized by dipping the entire wafer into an aqueous solution of potassium dichromate (12 mM) and hydrochloric acid (60 mM). Over these patterned silver chloride electrodes is placed an ammonium ion sensitive membrane. The membrane material is made by dissolving low molecular weight PVC (Sigma) and high molecular weight carboxylated PVC (Type Geon, Goodrich) (1:1 w/w) in a solvent system of cyclohexanone, propiophenone, and N-methylpyrrolidone (1:1:1 v/v/v) to a total solids content of 10 g/dL of solution. Dissolution is accomplished by heating the mixture at 70.degree. C. for 30 minutes. To this mixture the plasticizer tris(2-ethylhexyl)phosphate (Fluka) is added, to provide a total solids content of 35 g/dL. The resulting mixture is then allowed to cool to 45.degree. C. and nonactin (Fluka) is added in the amount equivalent to 2 percent of the total solids in the mixture. At room temperature, 10-100 nL of this final material is microdispensed onto each of the silver chloride indicator electrodes on the wafer, overlapping on all sides by at least about 30 .mu.m. Curing is accomplished by placing the wafer on a 60.degree. C. hot-plate for 30 minutes. This process yields a stable, rugged structure having a thickness of about 15 .mu.m. The wafer is then washed and partially diced. The urease solution is prepared by adding 305 mg of Urease (Genzyme Cat#1661 Jack Bean Urease E.C. 3.5.1.5>300 units/mg specific activity, free ammonia<0.0002 mol/unit) to a sterile plastic tube, to which 2.20 g of 100 mM sodium phosphate buffer, pH 6.8 was added to the tube and gently mixed on ice. The Carbonic Anhydrase solution is prepared separately with 0.3 g of Carbonic Anhydrase (Sigma-Aldrich Cat No. C3934) added to 1 ml of 100 mM sodium phosphate buffer, pH 6.8 in a sterile plastic tube and mixed gently on ice. A PVA solution is prepared by adding 1.4500 g PVA (Polysciences Cat No. 04398 or Aldrich Cat No. 36,310-3) to 27.4900 g of deionized sterile water, which is mixed on a stirring plate at 150° C. then allowed to cool to room temperature.

A microdispensing solution is prepared by adding 2.33 g of the urease solution with 3.38 g of Latex (ELVACE Reichold Cat No. 40711-00), 0.58 mL of the carbonic anhydrase solution, 1.55 g of 100 mM sodium phosphate, pH 6.8, 1.12 g of PVA solution.

The following formulations can be loaded into a microsyringe assembly for the purpose of establishing ion-sensitive layers in a controllable manner. The microsyringe assembly is preferably equipped with 25 to 30 gauge needles (EFD Inc.) having an internal diameter of 150 .mu.m and an external diameter of 300 mu.m. Typically, the microsyringe needle, which includes an elongated member and a needle tip, is made of a metallic material, like stainless steel. Additional layers may be coated onto the needle to change its surface properties. Furthermore, other materials such as synthetic polymers may also be employed in manufacturing the main body of the needle, itself. Depending on the pretreatment of the electrode surface and the volume amount of fluid applied, membrane layers of a thickness ranging from about 1 to about 200 .mu.m can be obtained consistently.

Automated Microdispensing System

An important aspect of the microfabricating process described in the present invention is an automated system, which is able to microdispense precise and programmable amounts of the materials used in the sensors of interest. The microdispensing system is comprised of a vacuum chuck and a syringe, each of which are attached to separate means for altering one or more of the vertical, horizontal, lateral, or rotational displacement of these elements. For the sake of economy, it is sufficient to have means for changing the vertical displacement of the syringe so long as one can change the position of the vacuum chuck multidirectionally. The movements of both elements may be controlled via a personal computer. The position of the vacuum chuck may be reproducible within .+-0.13 microns or better in either x or y directions.

The drop sizes which can be dispensed reproducibly extends over a wide range. For volume sizes between about 5 to about 500 nanoliters (nL), the drops can be applied with a precision of about 5%. A solenoid having a 0.1% precision rating is sufficient for this purpose. The height of the tip of the syringe needle above the sensor should be between about 0.1 to about 1 mm, depending on the volume to be dispensed: generally, the smaller the volume of the drop, the lower the elevation of the needle from the sensor.

The precise alignment of the syringe needle with the preselected area of the sensor can be achieved optically by means of a camera and a reticle. Such an operation can be performed manually by an operator or automatically by means of a visual recognition system.

Volumetric Microdispensing of Fluids

It is useful, at this point, to consider the dynamics involved when a single drop of fluid is formed at and expelled from a needle As more fluid is expelled from the needle tip, the drop will grow in size until the gravitational force acting on the mass of the drop exceeds the opposing forces maintaining contact with the needle tip. These opposing forces include the adhesive forces between the needle tip and the fluid or liquid, and surface tension of the liquid itself. It is well established that at low liquid flow rates where discrete drop formation is complete, the drop volume is fixed. However, the volume may be changed by varying any of the fluid related parameters discussed above, or by changing the diameter of the needle tip thus changing the available surface area for fluid adhesion. For example, a hydrophopic polytetrafluoroethylene (PTFE) coating applied to the needle tip reduces the natural drop size of an aqueous based latex material by reducing the adhesive forces between the drop and the needle tip.

In circumstances where a controlled volume must be microdispensed onto a surface, it is possible to have the microsyringe tip positioned above the planar surface at a height which does not allow the drop to form completely (and then fall to the surface under the influence of gravity), but the partially formed drop actually contacts the surface and the new adhesive forces between the liquid and the surface begin to spread the drop. If the needle tip is now retracted in the Z-direction a sufficient distance away from the surface, then the cohesive forces of the liquid is overcome and a volume of liquid less than the fixed drop size will remain in contact with the surface. This technique can be used to dispense reproducibly any volume of liquid from about one-one thousandth of the fixed drop size and greater.

Fluid Compositions with Predetermined Surface Tension

The surface tension between a pure liquid and its vapor phase can be changed by adding reagents. For example, a fatty acid added to water reduces the surface tension, whereas added salts can increase surface tension.

The microdispensable fluid compositions of the present invention are prepared to have a controlled optimized surface tension. Suitable additives are used when necessary. The hydrophobicity or hydrophilicity of the fluid is controlled in the same manner. Where a cured membrane is required as the end product, the solids content and volatile solvents content are carefully adjusted. Moreover, the ratio of these components is also used to control the viscosity.

The preferred microdispensable compositions for the ammonium ion sensor comprises PVC polymer, plasticizers, ionophores and solvents with viscosities generally higher than those used for planar casting (e.g., spin-coating) of membranes. These higher viscosity compositions cure or dry without deformation of the membrane layer. Related problems, e.g., that of ensuring the homogeneity of the matrix at high viscosity and thus preventing phase separation of materials after time (i.e., considerations related to shelf-life) are also alleviated by these compositions. Other additives are also used to prevent long-term degradation of the membranes. Finally, the solvent system is selected to provide the appropriate surface tension and stability. For $NH_4^+$ sensors, the solids content (wt %) of plasticizer, PVC polymer, and ionophore are preferably 60-80%, 15-40% and 0.5-3%, respectively.

Methods for Tailoring the Surface Energy of a Planar Structure

In addition to the factors described above relating to controlled volumetric dispensing of fluids having an optimized surface tension associated with a prescribed composition, tailoring the surface free energy of the substrate, or surface onto which the fluid is dispensed, provides control over the final dimensions, especially the thickness, of the resulting layer. The resulting process is highly versatile, allowing the deposition of arrays of layers of varied composition and utility.

For establishing thick membranes, (e.g., 40-60 .mu.m thick), the surface is preferably tailored so that the contact angle which the microdispensed fluid makes with the surface is large. For example, before an aqueous latex membrane is microdispensed, the surface is first plasma treated with carbon tetrafluoride to yield a contact angle for water (control fluid) in the range 50°-70°.

Cartridge Construction:

The preferred embodiment provides cartridges and methods of their use for processing liquid samples to determine the presence or amount of an analyte in the sample.

Referring to the Figures, the cartridge of the present invention comprises a cover (two views), FIGS. 10, 11, a base, FIG. 13, and a thin-film adhesive gasket, FIG. 12, disposed between the base and the cover and securing them together. Specifically, the backside of the cover shown in FIG. 10 mates with the exposed face of the gasket of FIG. 12, and the backside of the gasket mates with the exposed face of the base of FIG. 13. Referring now to FIG. 10, the cover 1 is made of a rigid material, preferably plastic, and capable of repetitive deformation at flexible hinge regions 5, 9, 10 without cracking. The cover comprises a lid 2, attached to the main body of the cover by a flexible hinge 9. In operation, after introduction of a sample into the sample holding chamber 34, the lid can be secured over the entrance to the sample entry port 4, preventing sample leakage by means of deformable seal 11, and the lid is held in place by hook 3. The cover further comprises two paddles 6, 7, that are moveable relative to the body of the cover, and which are attached to it by flexible hinge regions 5, 10. In operation, when operated upon by a pump means, paddle 6 exerts a force upon an air bladder comprised of cavity 43, which is covered by thin-film gasket 21, to displace fluids within conduits of the cartridge. When operated by a second pump means, paddle 7 exerts a force upon the gasket 21, which can deform. The cartridge is adapted for insertion into a reading apparatus, and therefore has a plurality of mechanical and electrical connections for this purpose. It should also be apparent that manual operation of the cartridge is possible. Thus, after insertion of the cartridge into a reading apparatus, the reading apparatus transmits pressure onto a fluid-containing foil pack filled with approximately 130 uL of calibrant fluid located in cavity 42, rupturing the package upon spike 38, and expelling fluid into conduit 39, which is connected via a short transecting conduit in the base to the sensor conduit, 12. When the calibrant fluid contacts the sensors, they wet-up and establish a signal associated with the amount of calibrating ion or molecule in the fluid.

Referring to FIG. 12, thin-film gasket 21 comprises various holes and slits to facilitate transfer of fluid between conduits within the base and the cover, and to allow the gasket to deform under pressure where necessary. Holes 30 and 33 permit one or more urea sensors and one or more reference electrode that are housed within either cutaway 35 or 37, to contact fluid within conduit 12.

Referring to FIG. 13, conduit 34 is the sample holding chamber that connects the sample entry port 4 to first conduit 15 in the assembled cartridge. Cutaways 35 and 37 optionally houses a conductimetric sensor for determining the position of air-liquid boundaries. Recess 42 houses a fluid-containing package, e.g., a rupturable pouch, in the assembled cartridge that is pierced by spike 38 because of pressure exerted upon paddle 7 upon insertion into a reading apparatus. Fluid from the pierced package flows into the second conduit at 39 and then into conduit 12. An air bladder is comprised of recess 43 which is sealed on its upper surface by gasket 21. The air bladder is one embodiment of a pump means, and is actuated by pressure applied to paddle 6 which displaces air in conduit 40 and thereby displaces the sample from sample chamber 34 into conduit 15 and then 12.

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

The invention claimed is:

1. A device for detecting urea in a sample, comprising:
   (a) a sensor with which a sample suspected of containing urea may be brought into contact, the sensor comprising urease and carbonic anhydrase immobilized on at least a portion of a single electrode of said sensor, and
   (b) a detector system for processing signals from the sensor,
   wherein the device is configured to inhibit gas exchange from the sample to an air space in a region of the immobilized urease and carbonic anhydrase.

2. The device of claim 1 in which said sensor comprises an ammonium ion-selective sensor.

3. The device of claim 1 in which said sensor comprises a pH sensor.

4. The device of claim 1 in which said sensor comprises a carbon dioxide or bicarbonate sensor.

5. The device of claim 1 in which said sensor comprises a conductivity sensor.

6. The device of claim 1 further comprising a second sensor without said immobilized enzymes.

7. The device of claim 1 in which said sensor is selected from the group consisting of a potentiometric electrode, a conductimetric electrode, an optical sensor, or combinations thereof.

8. The device of claim 6 in which said second sensor is selected from the group consisting of an amperometric electrode, a potentiometric electrode, a conductimetric electrode, an optical sensor, or combinations thereof.

9. The device of claim 2 in which the ammonium ion-selective sensor includes an ammonium ionophore.

10. The device of claim 2 in which the ammonium ion-selective sensor includes nonactin.

11. The device of claim 2 in which the ammonium ion-selective sensor includes plasticized polymer.

12. The device of claim 1 in which the sensor comprises a potentiometric ammonium ion-selective electrode.

13. The device of claim 1 in which the urease and the carbonic anhydrase are immobilized in a layer, said layer comprising a water-permeable matrix.

14. The device of claim 13 in which the water-permeable matrix comprises a film-forming latex.

15. The device of claim 14 in which said film-forming latex comprises a copolymer of ethylene and vinylacetate.

16. The device of claim 1 in which at least one of the urease and the carbonic anhydrase is immobilized via a chemical cross-linking reagent.

17. The device of claim 1 in which at least one of the urease and the carbonic anhydrase is immobilized via physical absorption.

18. The device of claim 13 in which the layer further comprises a buffer.

19. The device of claim 18 in which said buffer is selected from the group consisting of phosphate, TRIS, HEPES, or combinations thereof.

20. The device of claim 14 in which said film-forming latex includes a buffer selected from the group consisting of phosphate, TRIS, HEPES, or combinations thereof.

21. A microfabricated sensing device for detecting urea in a sample comprising:
   (a) a substantially planar substrate having a patterned microelectrode surface,
   (b) a first layer over at least a portion of said substrate comprising a plasticized polymer and nonactin, and
   (c) a second layer positioned over at least a portion of said first layer, comprising a water-permeable matrix in which is included at least urease and carbonic anhydrase,
   wherein the urease and carbonic anhydrase are immobilized on at least a portion of a single electrode, and
   wherein the device is configured to inhibit gas exchange from a sample solution to an air space in a region of the urease and carbonic anhydrase.

22. The microfabricated sensing device of claim 21 in which said polymer is polyvinylchloride.

23. The device of claim 21 in which said patterned microelectrode surface establishes a potential in response to the presence of ammonium ions.

24. The device of claim 21 in which the urease and the carbonic anhydrase are immobilized in said water-permeable matrix.

25. The device of claim 21 in which said first and second layers are microdispensed.

* * * * *